(12) United States Patent
Katasho et al.

(10) Patent No.: US 9,714,445 B2
(45) Date of Patent: Jul. 25, 2017

(54) CHIP DEVICE FOR MANIPULATING OBJECT COMPONENT, AND METHOD USING THE SAME

(71) Applicant: SHIMADZU CORPORATION, Kyoto (JP)

(72) Inventors: Isao Katasho, Kyoto (JP); Tetsuo Ohashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/365,104

(22) PCT Filed: Nov. 5, 2012

(86) PCT No.: PCT/JP2012/078587
§ 371 (c)(1),
(2) Date: Jun. 13, 2014

(87) PCT Pub. No.: WO2013/094322
PCT Pub. Date: Jun. 27, 2013

(65) Prior Publication Data
US 2014/0370511 A1 Dec. 18, 2014

(30) Foreign Application Priority Data
Dec. 22, 2011 (JP) .................. 2011-282185

(51) Int. Cl.
*C12M 1/00* (2006.01)
*C12Q 1/68* (2006.01)
(Continued)

(52) U.S. Cl.
CPC ...... *C12Q 1/6806* (2013.01); *B01L 3/502761* (2013.01); *G01N 33/04* (2013.01);
(Continued)

(58) Field of Classification Search
CPC . C12Q 1/68; G01N 35/0098; B01L 3/502707; B01L 7/52
(Continued)

(56) References Cited

U.S. PATENT DOCUMENTS 3,313,358 A 4/1967 Postlewaite et al.
4,683,195 A 7/1987 Mullis et al.
(Continued)

FOREIGN PATENT DOCUMENTS

EP 389063 9/1990
JP H02-289596 11/1990
(Continued)

OTHER PUBLICATIONS

"International Search Report (Form PCT/ISA/210) of PCT application", mailed on Mar. 19, 2013, with English translation thereof, p. 1-p. 4.
(Continued)

*Primary Examiner* — Narayan Bhat
(74) *Attorney, Agent, or Firm* — Jianq Chyun IP Office

(57) ABSTRACT

A chip device for manipulating an object component is described, in which multiple liquid substances such as reagents required for a series of manipulations on a sample are stably secured in separated states throughout the manipulations within the device. The chip device includes a manipulation chip, magnetic particles, and a magnetic field application means. The manipulation chip includes a substrate, a groove formed in the surface of the substrate, and a manipulation medium accommodated in the groove such that gel phases and aqueous liquid phases are alternately disposed in the longitudinal direction of the groove and are in contact with each other. The magnetic particles are for capturing and carrying the object component. The magnetic field application means is capable of moving the magnetic
(Continued)

particles in the longitudinal direction of the groove in the substrate by the application of a magnetic field to the substrate.

20 Claims, 16 Drawing Sheets

(51) Int. Cl.
*H02K 44/00* (2006.01)
*H02K 44/08* (2006.01)
*H02K 44/02* (2006.01)
*G01N 33/04* (2006.01)
*G01N 33/487* (2006.01)
*B01L 3/00* (2006.01)
*B01L 7/00* (2006.01)
*G01N 35/00* (2006.01)

(52) U.S. Cl.
CPC ....... *G01N 33/48707* (2013.01); *H02K 44/02* (2013.01); *B01L 3/502707* (2013.01); *B01L 7/52* (2013.01); *B01L 2200/0668* (2013.01); *B01L 2200/0673* (2013.01); *B01L 2300/0816* (2013.01); *B01L 2300/0864* (2013.01); *B01L 2300/0867* (2013.01); *B01L 2300/165* (2013.01); *B01L 2400/043* (2013.01); *G01N 35/0098* (2013.01); *Y10T 29/49* (2015.01)

(58) Field of Classification Search
USPC .............. 435/6.12, 174; 29/592; 417/50; 422/507
See application file for complete search history.

(56) References Cited

U.S. PATENT DOCUMENTS

| | | |
|---|---|---|
| 4,683,202 A | 7/1987 | Mullis |
| 4,786,600 A | 11/1988 | Kramer et al. |
| 4,800,159 A | 1/1989 | Mullis et al. |
| 4,965,188 A | 10/1990 | Mullis et al. |
| 5,354,688 A | 10/1994 | Francis et al. |
| 5,409,818 A | 4/1995 | Davey et al. |
| 5,455,166 A | 10/1995 | Walker |
| 5,494,810 A | 2/1996 | Barany et al. |
| 6,406,604 B1 | 6/2002 | Guzman |
| 6,951,722 B2 | 10/2005 | Mukai et al. |
| 2004/0018611 A1* | 1/2004 | Ward et al. ............ 435/287.2 |
| 2010/0084270 A1* | 4/2010 | Vulto ............ B01L 3/502753 204/461 |
| 2013/0043150 A1 | 2/2013 | Ohashi |

FOREIGN PATENT DOCUMENTS

| | | | |
|---|---|---|---|
| JP | 2843586 | | 1/1999 |
| JP | 2003500645 | | 1/2003 |
| JP | 3433929 | | 8/2003 |
| JP | 2004-045410 | | 2/2004 |
| JP | 2006-061031 | | 3/2006 |
| JP | 2006-518221 | | 8/2006 |
| JP | 2007-315936 | | 12/2007 |
| JP | 2008-039541 | | 2/2008 |
| JP | 2008-517259 | | 5/2008 |
| JP | 2008-233002 | | 10/2008 |
| JP | 2009-534653 | | 9/2009 |
| JP | 4353900 | | 10/2009 |
| JP | WO 2011/135881 | * | 3/2011 |
| JP | 2011-232260 | | 11/2011 |
| WO | 8810315 | | 12/1988 |
| WO | 0071999 | | 11/2000 |
| WO | 2004024327 | | 3/2004 |
| WO | 2004080597 | | 9/2004 |
| WO | 2006042838 | | 4/2006 |
| WO | 2007120241 | | 10/2007 |

OTHER PUBLICATIONS

Park et al., "A cell-free protein-producing gel", Nature Materials, Mar. 29, 2009, pp. 432-437, vol. 8.
Park et al., "High-yield cell-free protein production from P-gel", Nature Protocols, Nov. 12, 2009, pp. 1759-1770, vol. 4, No. 12.

* cited by examiner

CHIP DEVICE FOR MANIPULATING OBJECT COMPONENT, AND METHOD USING THE SAME

CROSS-REFERENCE TO RELATED APPLICATION

This application is a 371 application of an International PCT application serial no. PCT/JP2012/078587 filed on Nov. 5, 2012, which claims priority benefits of Japan Patent Application No. 2011-282185 filed on Dec. 22, 2011. The entirety of each of the above-mentioned patent applications is hereby incorporated by reference herein and made a part of this specification.

FIELD OF THE INVENTION

This invention relates to a μTAS (Micro-Total Analysis Systems) device.

DESCRIPTION OF RELATED ART

Japanese Unexamined Patent Application Publication (Translation of PCT Application) No. 2009-534653 (Patent Literature 1) discloses a device for manipulating a droplet on a substrate surface using EWOD (electrowetting on dielectrics) technology and performing division, mixture, detection, fractionation, and storage of a sample. Use of a magnetically responsive bead capable of binding nucleic acid is also disclosed.

The specification of U.S. Pat. No. 6,406,604 (Patent Literature 2) discloses a multi-analysis chip capable of performing affinity concentration and purification through capillary electrophoretic separation by immobilizing an antibody on a portion of a separation channel which is formed on a substrate.

The specification of Japanese Patent No. 4353900 (Patent Literature 3) discloses a device in which a flow path of an upper substrate and a flow path of a lower substrate intersect each other, and at the intersection, the two flow paths are in contact with each other through a porous member such as a porous silicon membrane.

Japanese Patent Publication No. 2008-233002 (Patent Literature 4) discloses a reaction chip, wherein a well-shaped reaction vessel and a flow path are formed on a substrate, and reaction reagent-immobilized magnetic particles are disposed in the well-shaped reaction vessel.

Japanese Patent Publication No. 2006-61031 (Patent Literature 5) discloses an analytical processing chip in which multiple wells are connected by a flow path. The analytical processing chip is capable of purifying a nucleic acid by applying a magnetic field and moving a magnetic material, to which the nucleic acid is attached, from a first purification well to a second purification well through the flow path.

Japanese Unexamined Patent Application Publication (Translation of PCT Application) No. 2008-517259 (Patent Literature 6) discloses a device that utilizes magnetic particles to automatically and comprehensively analyze DNA or proteins of a sample under measurement in a card that has a small passage with a geometric shape for receiving reagents.

Japanese Patent Publication No. 2007-315936 (Patent Literature 7) discloses a microchip that can control the flow of a fluid by applying pressure to a fluid control section which is provided with a wall having a notch for cutting off a flow path disposed on a substrate.

Japanese Unexamined Patent Application Publication (Translation of PCT Application) No. 2006-518221 (Patent Literature 8) discloses a sample processing tubule having at least three segments that are fluidly isolated by breakable seals and contain reagents. The sample processing tubule is capable of continuously carrying out processes from nucleic acid extraction from cells to the analysis by gene amplification reaction in one tubule.

PRIOR ART LITERATURE

Patent Literature

Patent Literature 1: Japanese Unexamined Patent Application Publication (Translation of PCT Application) No. 2009-534653
Patent Literature 2: Specification of U.S. Pat. No. 6,406,604
Patent Literature 3: Specification of Japanese Patent No. 4353900
Patent Literature 4: Japanese Patent Publication No. 2008-233002
Patent Literature 5: Japanese Patent Publication No. 2006-61031
Patent Literature 6: Japanese Unexamined Patent Application Publication (Translation of PCT Application) No. 2008-517259
Patent Literature 7: Japanese Patent Publication No. 2007-315936
Patent Literature 8: Japanese Unexamined Patent Application Publication (Translation of PCT Application) No. 2006-518221

SUMMARY OF THE INVENTION

Problem to be Solved by the Invention

Because of the advantages of minimizing the sample, improving throughput of the analysis through multi-analysis, etc., a number of studies have been made with respect to the μTAS (Micro-Total Analysis Systems) device, which forms a flow path on the chip, integrates functions such as isolation and detection, and performs analyses. In order to perform complex analyses, such as multi-sample measurement with common detector, analysis after purification, and mixture of multiple reagents that cannot be used simultaneously, it is necessary to make several flow paths intersect each other. However, the conventional methods require multiple pumps or valves, which complicate the structure of the device, and thus cannot take full advantage of μTAS.

The device of Patent Literature 1 is for performing many manipulations such as fractionation and reaction with respect to a droplet on a substrate surface. Because the manipulation of the droplet is based on EWOD, complex electrical control is necessary and the manipulation is greatly affected by charge and the surface state, which impairs the stability of droplet manipulation. In addition, the reagent solution cannot be stably secured on the device. Because the reagent solution needs to be supplied from outside the device every time, there is a possibility of contamination.

The device of Patent Literature 2 is mainly used for performing affinity concentration through immobilized antibody, etc., and purification through electrophoretic separation and does not take the reaction in the flow path into consideration. Because the flow path can only be filled with one type of solution or one type of gel, the device performs very limited manipulations.

The device of Patent Literature 3 is a system that stores the reagent in a dry state in the flow path and allows a solution to flow into the flow path. Therefore, the reagent cannot be secured in a solution state. Although a porous film is provided in a connecting portion of the intersecting flow paths, the film is not prepared for filtering fine particles and thus cannot secure the reagent solution. Further, pumps and valves are required in order to operate the device.

Regarding the devices of Patent Literatures 4, 5, 6, and 7, essentially the liquid moves through the flow path, and therefore, it is not possible to store the reagent in the solution state in the device.

In the device of Patent Literature 8, reagent solutions are separated by seals to be secured. However, when the sample passes through the reagent solutions, it is necessary to break the seals that separate the reagent solutions, which results in movement of the liquid in the tube.

Therefore, an object of this invention is to provide a device, in which a plurality of liquid materials such as reagents required for a series of manipulations on a sample are stably secured in separated states throughout the manipulations. A further object of this invention is to provide a method for manipulating a sample, which is capable of performing a series of processes all in sealed states with good operability in a device that contains a plurality of liquid materials required for the series of processes.

Solution to the Problem

The inventors found that the objects of this invention can be achieved by accommodating a plurality of aqueous liquids that are separated by gel materials in a plurality of grooves formed in a substrate and using magnetic particles that can be present in the aqueous liquids accommodated in the grooves and a magnetic field application means that can be operated from outside the substrate, and thus accomplished this invention.

This invention includes the following items.

Item 1 is a chip device adapted for manipulating an object component, which includes: a manipulation chip including a substrate, a groove formed in a surface of the substrate, and a manipulation medium accommodated in the groove such that gel phases and aqueous liquid phases are alternately arranged in the longitudinal direction of the groove and are in contact with each other;
magnetic particles for capturing and transporting the object component; and
a magnetic field application means capable of moving the magnetic particles in the longitudinal direction of the groove in the substrate by applying a magnetic field to the substrate.

FIG. 1 shows an example of a basic structure of the manipulation chip in item 1. FIG. 11 shows an example of use of the chip device that includes the manipulation chip.

Item 2 is the chip device of item 1 in which among the aqueous liquid phases, the aqueous liquid phase accommodated at a position closest to one end or the other end of the groove is to be initially supplied with a sample containing the object component.

The aqueous liquid phase to be initially supplied with the sample in item 2 is exemplified by 1a in FIG. 1, etc.

Item 3 is the chip device of item 1 or 2 in which the groove is composed of a main groove and a branching groove that branches from the main groove.

The branching form regarding the above (3) is illustrated in FIG. 3 and FIG. 4.

Item 4 is the chip device of item 3 in which the aqueous liquid phase accommodated at a position closest to the end of the groove on the main groove side is to be initially supplied with the object component.

Item 5 is the chip device of item 3 in which the aqueous liquid phase accommodated at a position closest to the end of the groove on the branching groove side is to be initially supplied with the object component.

Item 6 is the chip device of item 1 or 2, wherein the groove is composed of a plurality of grooves that intersect each other in a grid pattern.

The intersection pattern regarding item 6 is illustrated in FIG. 5.

Item 7 is the chip device of any one of items 1 to 6 in which a portion of the surface of the groove, which is in contact with the gel phases, has been subjected to a hydrophobic treatment.

Item 8 is the chip device of any one of items 1 to 7 in which a portion of the surface of the groove, which is in contact with the aqueous liquid phases, has been subjected to a hydrophilic treatment.

Item 9 is the chip device of any one of items 1 to 8 in which the groove has a width of 0.005 mm to 10 mm and a depth of 0.005 mm to 5 mm.

Item 10 is the chip device of any one of items 1 to 9 in which a cover is provided on the surface of the substrate on the side where the groove is formed.

Item 11 is the chip device of item 10 in which the cover includes a hole that penetrates the cover to communicate with the gel phase located at least one end of the groove.

The manipulation chip in the chip device of item 11 is illustrated in FIG. 6, etc.

Item 12 is the chip device of any one of items 4 and 7-11 in which the magnetic field application means includes a plurality of magnets that are substantially parallel to the surface of the substrate and are disposed in a one-dimensional array or a two-dimensional array; in a state that the plurality of magnets are attracted to each other, the plurality of magnets are movable substantially parallel to the surface of the substrate and in the longitudinal direction of the main groove; and a separation auxiliary tool is disposed on a path of the magnets and at a branch point between the main groove and the branching groove for separating the plurality of magnets.

Forms of the magnet and the separation auxiliary tool in the chip device of item 12 are illustrated in FIG. 16.

Item 13 is the chip device of any one of items 1 to 12 in which the aqueous liquid phases include a phase selected from the group consisting of a nucleic acid extraction solution phase, a nucleic acid cleaning solution phase, and a nucleic acid amplification reaction solution phase.

Item 14 is a method for manufacturing a manipulation chip included in the chip device of any one of the above items 1 to 13, including the following processes:
(i) a process of preparing a gel phase section in which a plurality of gel blocks are disposed apart from each other in the longitudinal direction of the groove formed in the substrate; and
(ii) a process of preparing an aqueous liquid phase section by disposing an aqueous liquid in a groove space adjacent to the gel phase section.

The method of the above item 14 is schematically illustrated in FIG. 10.

Item 15 is the method of item 14 which further includes (iii) a process of disposing the cover on the surface of the substrate on the side where the groove is formed.

Item 16 is a method for manipulating the object component with use of the chip device of any one of item 1 to 13, including the following processes:
(i) a process of obtaining an aqueous liquid mixture including a sample that contains the object component, magnetic particles, and the aqueous liquid in the aqueous liquid phase located at one end of the manipulation chip;
(ii) a process of generating a magnetic field by the magnetic field application means and transporting the magnetic particles together with the object component from the phase of the aqueous liquid mixture at an endmost position to the adjacent aqueous liquid phase through the gel phase;
(iii) a process of performing a desired treatment in the aqueous liquid phase;
(iv) a process of generating a magnetic field by the magnetic field application means and transporting the magnetic particles together with the object component from the aqueous liquid phase to another aqueous liquid phase;
(v) a process of performing a desired treatment in the another aqueous liquid phase;
(vi) a process of reiterating the processes (iv) and (v) as required; and
(vii) a process of transporting the magnetic particles together with the object component to the aqueous liquid phase located at the other end of the manipulation chip.

The method of the above item 16 is schematically illustrated in FIG. 11.

Item 17 is the method of item 16 in which a plurality of manipulation chips are provided and the transportation is performed simultaneously by the magnetic particles in the plurality of manipulation chips.

A device, in which the plurality of manipulation chips of the above item 17 are integrated, is illustrated in FIG. 13.

Item 18 is the method of item 16 or 17 in which the object component is a nucleic acid;
in the process (i), the aqueous liquid contained in the aqueous liquid mixture in the phase located at the one end is a liquid that releases the nucleic acid and binds or adsorbed the nucleic acid on the magnetic particles, and nucleic acid extraction is performed in the aqueous liquid; and
in the processes (ii) to (vi), at least one of the aqueous liquid phases includes a cleaning solution for the magnetic particles, and nucleic acid purification is performed by removing impurities that accompany the released nucleic acid in the cleaning solution.

Item 19 is the method of item 18 in which in the process (vii), the aqueous liquid phase located at the other end includes a nucleic acid amplification reaction solution, and amplification of a target nucleic acid in the purified nucleic acid is performed in the nucleic acid amplification reaction solution.

Item 20 is the method of item 19 in which a product of the nucleic acid amplification reaction is detected in real time.

Effects of the Invention

This invention can provide a device that is compact and requires low running costs, in which a plurality of liquid materials such as reagents required for a series of manipulations on a sample are respectively stably secured in separated states throughout the manipulations. This invention also achieves a method for manipulating a sample, which is able to perform a series of processes all in sealed states with good operability in a device containing a plurality of liquid materials required for the series of processes.

DESCRIPTION OF THE EMBODIMENTS

[1. Manipulation of Object Component]

[1-1. Object Component]

An object component to be manipulated in a chip device of this invention is not particularly limited as long as the object component is a component, regardless of biological component or non-biological component, which can usually be manipulated in an aqueous liquid or an emulsion. The biological components include biological molecules such as nucleic acids (including DNA and RNA), proteins, lipids, and sugars, etc. The non-biological components include non-biological molecules such as artificial (either chemical or biochemical) modifications of the aforesaid biological molecules, labeled bodies, and mutants, non-biological molecules derived from natural products, and any other components that can be manipulated in an aqueous liquid.

Generally, the object component can be provided in the form of being contained in a sample. Such a sample can be an organism-derived sample, such as animal and plant tissues, body fluids, and excreta, etc., or a biomolecule-containing product, such as cells, protozoa, fungi, bacteria, and viruses, etc., for example. The body fluids include blood, sputum, cerebrospinal fluid, saliva, and milk, as well as combinations thereof. The excreta include feces, urine, and sweat, as well as combinations thereof. The cells include white blood cells and platelets in the blood, buccal cells, and exfoliated cells of other mucosal cells, as well as combinations thereof. These samples may be obtained as clinical swabs. Further, the above samples may be prepared in the form of, for example, a cell suspension, a homogenate, or a mixture with a cell lysate, etc.

Also, the sample containing the object component may be obtained by performing a treatment of modification, labeling, fragmentation, or mutation on the above samples.

The sample containing the object component may also be prepared by performing a suitable pre-treatment on the above samples in advance. The pre-treatment is for example to extract, separate, or purify the object component or a substance containing the object component from the sample containing the object component. Since such a pre-treatment can be carried out inside the chip device of this invention, it is not necessarily required to perform the pre-treatment in advance before supplying the pre-treatment to the chip device. By carrying out the pre-treatment in the chip device of this invention, the problem of contamination, which is usually a concern in the pre-treatment of the sample, can be avoided.

[1-2. Manipulation]

[1-2-1. Embodiment of Manipulation]

Figure 1:
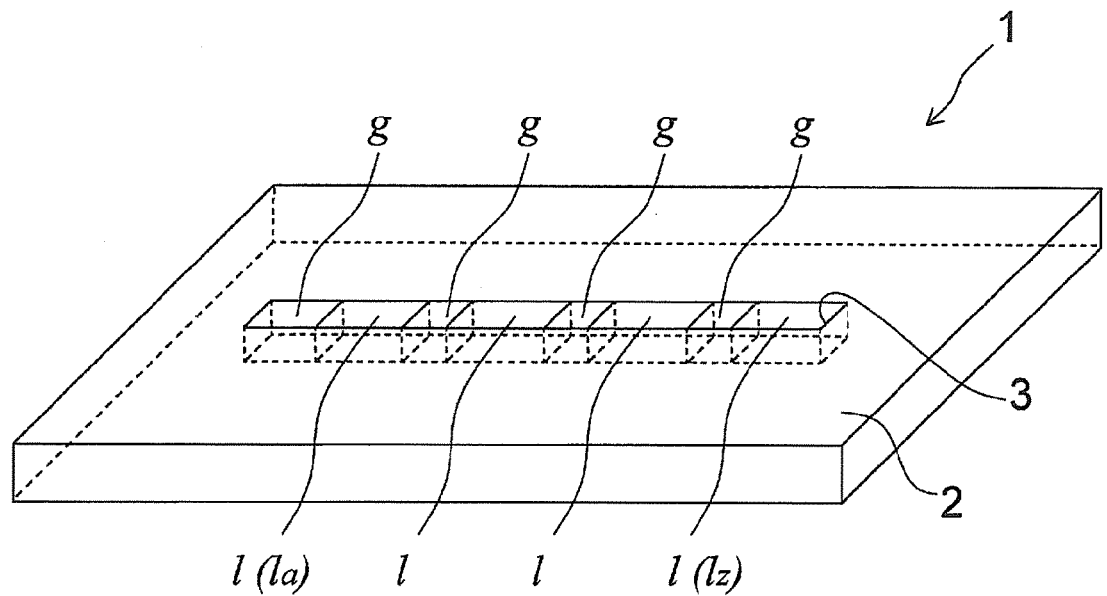
FIG. 1 shows a perspective view of a basic structure of a manipulation chip in a chip device of this invention.

In the chip device of this invention, the sample containing the object component is supplied to the manipulation chip shown in FIG. 1, in which the object component is then manipulated. The manipulation of the object component in this invention includes supplying the object component for various treatments and transporting the object component between multiple environments for performing various treatments.

In a manipulation chip 1, a diplophase, formed by alternately arranging a phase g composed of a gel and a phase l composed of an aqueous liquid, is accommodated in a groove 3 formed in a substrate 2 to serve as a manipulation medium. Details will be described later with reference to FIG. 1. The aqueous liquid is used mainly to create an environment for performing the treatment on the object component.

Therefore, more specifically, the manipulation of the object component in this invention includes supplying the object component for treatments mainly in the aqueous liquid and, through the gel phase, transporting the object component between multiple environments for performing the treatments.

[1-2-2. Treatment of Object Component]

The treatments supplied with the object component include those involving a material change of the object component and those involving a physical change.

The treatments involving the material change of the object component include any treatment that results in a new different material by bond formation or cleavage between substrates, specifically including chemical reactions and biochemical reactions.

The chemical reactions include any reaction involving combination, decomposition, oxidation or reduction, and generally include reactions that take place in the aqueous liquid in this invention. The biochemical reactions include any reaction that involves the material change of a biological material, which is usually referred to as an in-vitro reaction. For example, such reactions are based on synthesis system, metabolic system or immune system of biological materials such as nucleic acid, protein, lipid, and sugar.

The treatments involving the physical change of the object component include any treatment that does not cause the aforementioned material change, and more specifically include modification (for example, in a situation that the object component is a biopolymer containing a nucleic acid or a protein, or other like polymer), dissolution, mixture, emulsification, and dilution of the object component.

Therefore, through the treatments of this invention, it is possible to perform processes of extraction, purification, synthesis, dissolution, separation, recovery, and analysis of the object component, by which the object component can eventually be isolated, detected, and identified, etc.

The treatments of this invention are not limited to the intended treatment (treatment in the processes for directly achieving the effects of isolating, detecting, and identifying the object component) and properly include a pre-treatment and/or a post-treatment associated with the intended treatment. For example, in the situation where the object component is a nucleic acid, processes, such as nucleic acid amplification reaction, or nucleic acid amplification reaction and analysis of an amplification product, may be performed, for which extraction (cell lysis) of the nucleic acid from a nucleic acid-containing sample and/or its purification (cleaning) are necessary pre-treatments. Recovery of the amplification product, etc., may be performed as the post-treatment.

[1-2-3. Transportation of Object Component]

The object component is transported by means of the magnetic particles and a magnetic field application means. The magnetic particles are present in the manipulation chip during the manipulation, and move in the manipulation chip in a state that the object component is captured by them through binding or adsorption on their surfaces, so as to transport the object component. The magnetic particles can be dispersed in the aqueous liquid phase in the manipulation chip. The magnetic particles are aggregated in the aqueous liquid phase usually by a magnetic field that is generated by the magnetic field application means outside the manipulation chip. The aggregated magnetic particles can move in accordance with a variation of the magnetic field generated by the magnetic field application means outside the manipulation chip. The aggregated magnetic particles can move in the gel phase. By utilizing the thixotropic properties (thixotropy) of the gel, which will be described later in 3-2-3, the aggregated magnetic particles can pass without disrupting the gel phase. In the gel, the aggregated magnetic particles are accompanied by the object component through binding or adsorption. The aggregations of the magnetic particles are precisely coated with a very small amount of aqueous liquid.

That is, there may be components other than the object component. Nevertheless, the amount of the aqueous liquid coated thereon is very small. Therefore, the object component can be transported very efficiently.

[2. Manipulation Chip]

[2-1. Structure of Manipulation Chip]

Figure 2:
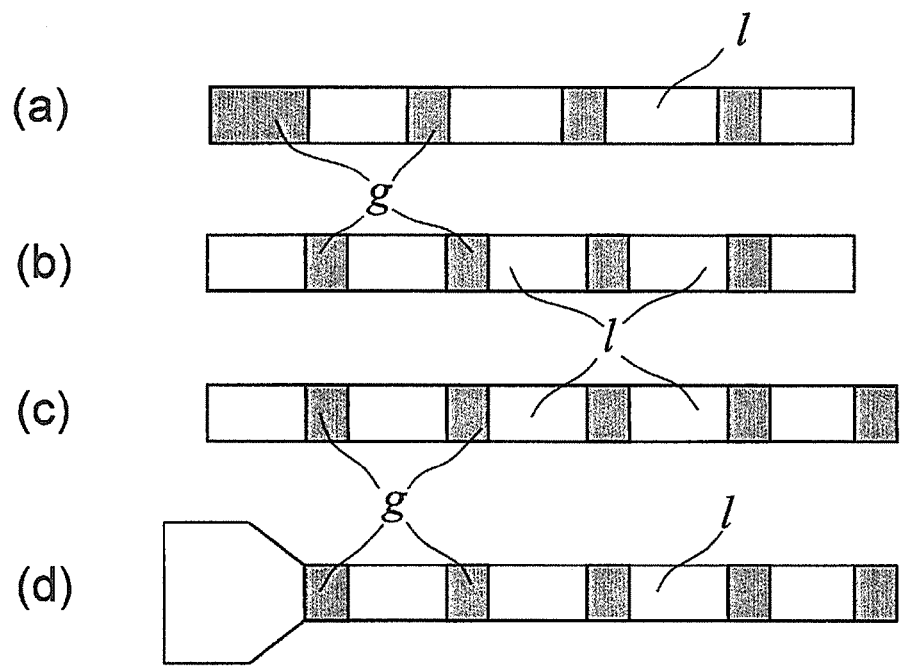
FIG. 2 shows a plan view of an arrangement pattern of gel phases and aqueous liquid phases accommodated in a groove formed in a substrate of the manipulation chip.
Figure 3:
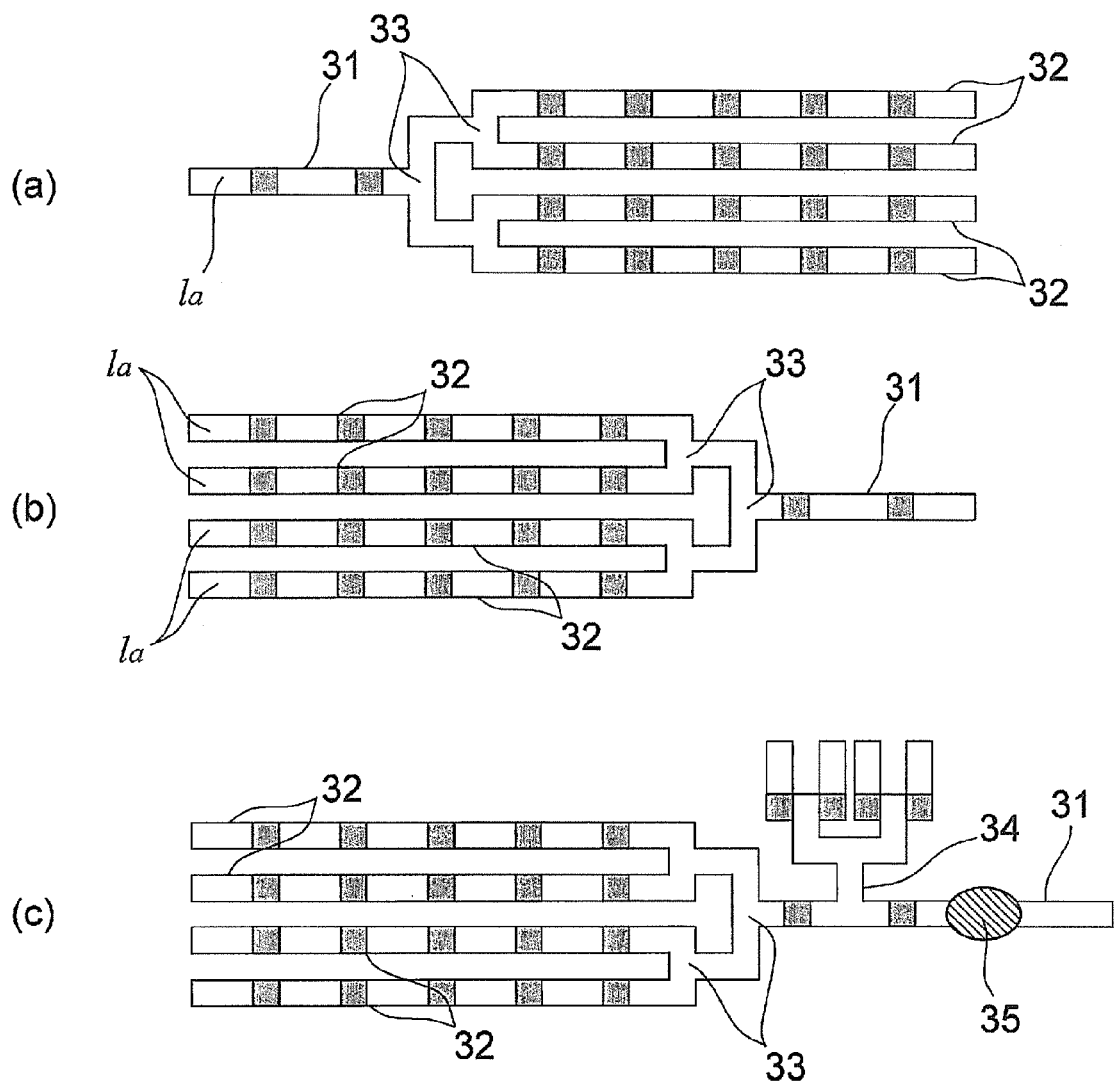
FIG. 3 shows plan views of examples of branching of the groove formed in the substrate of the manipulation chip as well as examples of the arrangement pattern of the gel phases and aqueous liquid phases accommodated in the groove.
Figure 4:
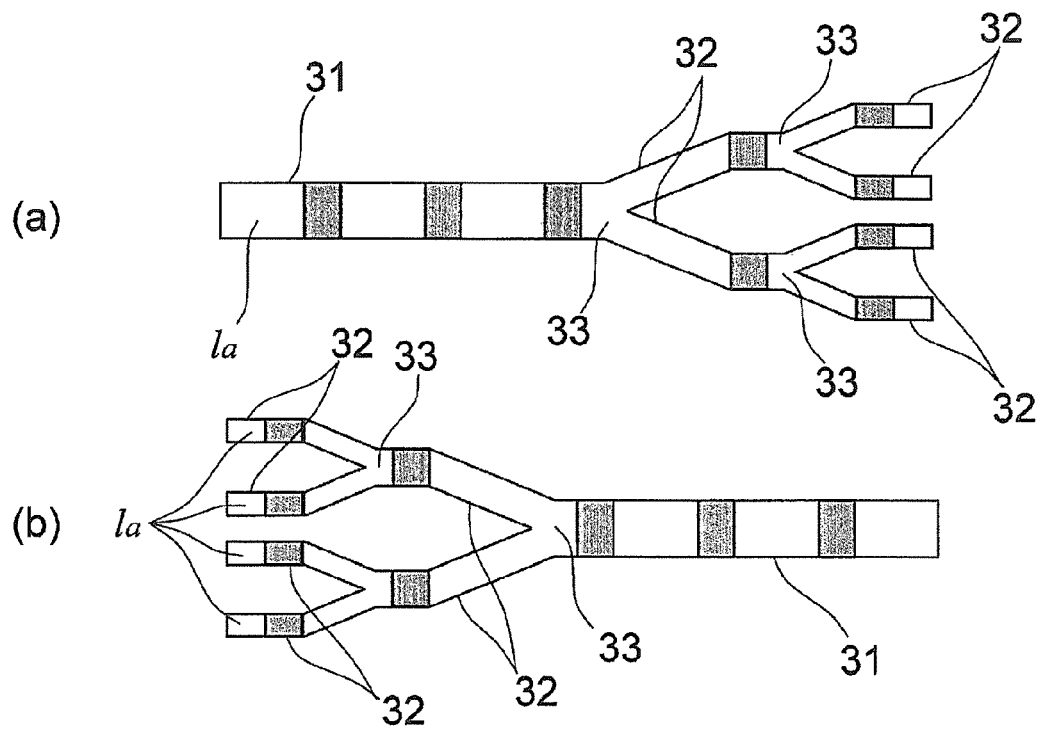
FIG. 4 shows plan views of examples of branching of the groove formed in the substrate of the manipulation chip as well as examples of the arrangement pattern of the gel phases and aqueous liquid phases accommodated in the groove.

The device of this invention includes a manipulation chip having a basic structure as shown in FIG. 1. The manipulation chip 1 includes a substrate 2. A groove 3 is formed in the substrate 2. A manipulation medium is accommodated in the groove 3 such that the gel phases g and the aqueous liquid phases l are alternately disposed in the longitudinal direction of the groove 3 and are in contact with each other. FIG. 1 shows a phase arrangement pattern in which one end of the groove is provided with the gel phase g while the other end provided with the aqueous liquid phase l. However, either of the gel phase g and the aqueous liquid phase l can be disposed at the ends of the groove. For example, FIG. 2a-c shows several arrangement patterns of the gel phases g and the aqueous liquid phases l (other elements of the substrate are omitted, as in the following FIGS. 3-5). However, this invention is not limited thereto. Among the aqueous liquid phases accommodated in the groove, generally the aqueous liquid phase closest to either end of the groove is the one to which the object component should be initially supplied, namely, the one that constructs a manipulation environment for the initially supplied object component. Described below is a situation where the aqueous liquid phase to which the object component should be initially supplied is assigned with the reference numeral 1a. Moreover, a situation where the aqueous liquid phase closest to the end opposite to the aqueous liquid phase 1a is assigned with the reference numeral 1z is also described.

[2-2. Shape of Groove]

Moreover, regarding the groove shape, the entire groove may have a substantially uniform width as shown in FIG. 2a-c, or the groove width may be greater at an end portion of the groove as shown in FIG. 2d. So is the depth of the groove. The groove shape shown in FIG. 2d has the advantages that it is easy to introduce the object sample into the manipulation chip, and the amount of the object sample to be introduced can be increased. In the groove having the greater groove width, the aqueous liquid may or may not be accommodated before the object sample is introduced.

Figure 7:
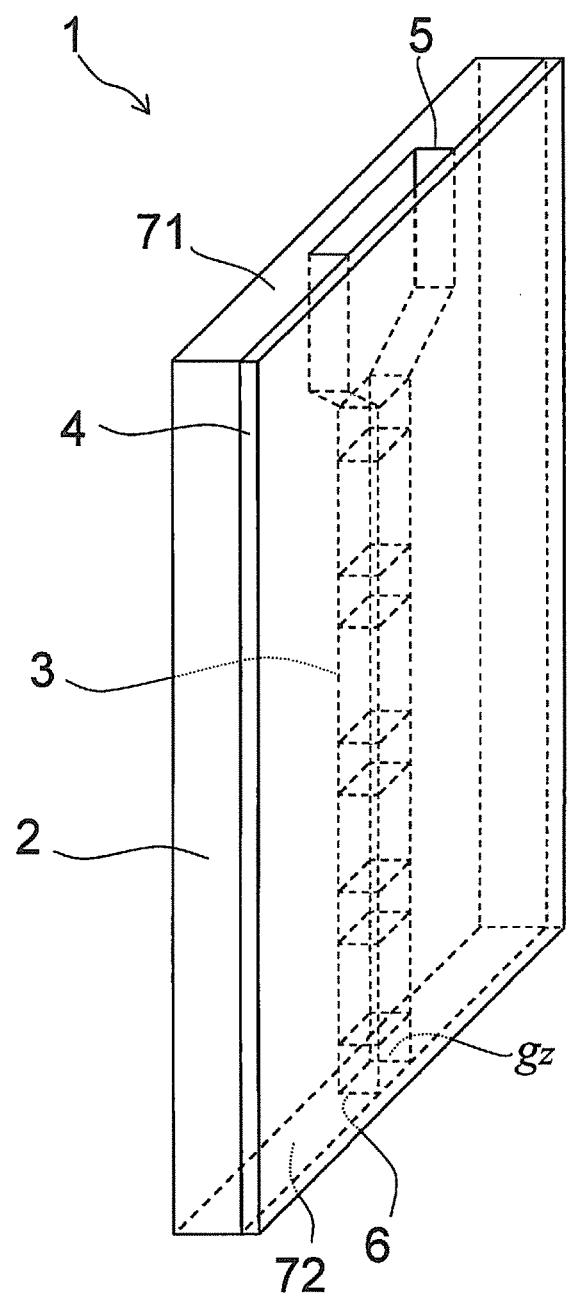
FIG. 7 shows a perspective view of another example of the manipulation chip with the cover plate disposed on the surface of the substrate.

Further, in FIG. 1, the ends of the groove 3 in its longitudinal direction are disposed inwardly with respect to end surfaces of the substrate 2. Nevertheless, the ends of the groove 3 in the longitudinal direction may alternatively reach the end surfaces 71 and 72 of the substrate 2, as shown in FIG. 7 which will be described later.

The pattern in which the groove is formed is not particularly limited, and the groove may have a linear shape or a curved shape and the groove may branch or not branch. In a situation that the groove has branches, as shown in FIG. 3a-c or FIG. 4a-b for example, the groove includes a main groove 31 and a plurality of branching grooves 32 that branch from the main groove 31. In FIG. 3c, the main groove 31 further includes a branching groove 34. In addition to the disclosure of the figures, the branching grooves 32 may branch in any stage. Regarding the form of branching, two branching grooves 32 may form a straight angle at a branching point as shown in FIG. 3a-b, the main groove 31 and the branching groove 34 may form a right angle at the branching point as shown in FIG. 3c, or two branching grooves 32 may form an acute angle at the branching point as shown in FIG. 4a-b.

Figure 5:
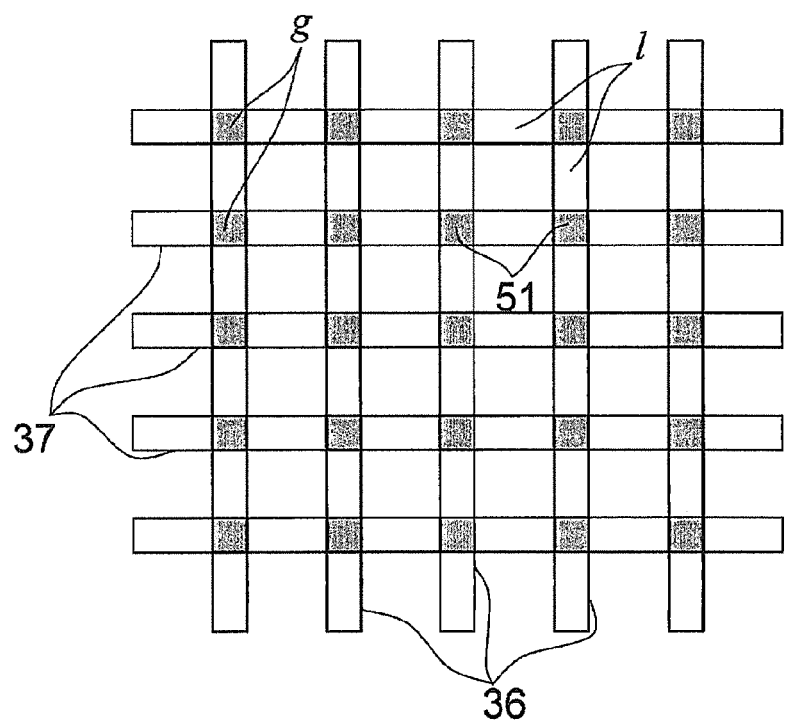
FIG. 5 shows a plan view of an example of intersection of the grooves formed in the substrate of the manipulation chip as well as an example of the arrangement pattern of the gel phases and aqueous liquid phases accommodated in the grooves.

Besides, a plurality of grooves may be formed to intersect with each other in a grid pattern as shown in FIG. 5, for example. More specifically, a plurality of grooves 36 that extend in the longitudinal direction and a plurality of grooves 37 that extend in a transverse direction may be disposed in an intersection pattern.

The groove has a size of 0.005 mm to 10 mm in width and 0.005 mm to 5 mm in depth. Below the above ranges, the operability tends to be affected adversely. Above the above ranges, the diplophase of the gel phase and aqueous liquid phase making up the manipulation medium tends to be disturbed by the gravity and impact from outside.

[2-3. Size and Material of Substrate]

The size of the substrate is not particularly limited. The substrate size in the devices that have been used in the field of μTAS (Micro-Total Analysis Systems) heretofore can be adopted, which is 10 mm to 500 mm longitudinally, 10 mm to 500 mm transversely, and 0.2 mm to 10 mm in thickness, for example.

The material of the substrate is not particularly limited, and one of ordinary skill in the art may take various physical properties or the workability into consideration to determine the appropriate material for the substrate. The material may be a resin material, such as polyethylene, polypropylene, fluorine resin (Teflon™), polyvinyl chloride, polystyrene, polycarbonate, acrylonitrile-butadiene-styrene copolymer (ABS resin), acrylonitrile-styrene copolymer (AS resin), acrylic resins, polyvinyl acetate, polyethylene terephthalate, polyether ether ketone (PEEK resin), epoxy resin-based negative photoresist (SU8), polydimethylsiloxane (PDMS resin), and cyclic polyolefin, for example. The resin material is preferred as providing a high robustness that the phases in the substrate are hardly disturbed even if the chip device is dropped or bent.

In addition to the above resin material, ceramic, glass (quartz glass, for example), quartz, and metal, etc. can also be used.

From the viewpoint of preventing mixing air bubbles into the groove in the process of fabricating the manipulation chip, it is also possible to use a material that can occlude gas (specifically, a porous coordination polymer).

[2-4. Physical Property of Substrate and Surface Treatment]

Considering the visibility during manipulation or the situation of performing an optical detection (specifically, measurement of variation of absorbance, fluorescence, chemiluminescence, bioluminescence, and refractive index, etc.) from the outside of the substrate, it is preferred that the material of the substrate has light permeability. From this viewpoint, quartz glass is particularly preferable.

In view of operability, it is preferred that a conveying surface, which constitutes an inner wall of the groove farmed in the substrate, is a smooth surface. In particular, preferably the surface roughness Ra is 0.1 μm or less. For example, as a permanent magnet is brought close to the substrate from the outside of the substrate, the magnetic particles accompanied by the object component are moved due to the variation of the magnetic field. Since the surface roughness Ra of the conveying surface is 0.1 μm or less, when the magnetic particles are pressed against the conveying surface and moved thereon, they have sufficient followability with respect to the varying magnetic field.

In addition, the surface of the inner wall of the groove 3 may be applied with a surface treatment as appropriate. Considering the operability of the gel phase and the stability of phase fixation, for example, a portion of the inner wall surface of the groove, which is in contact with the gel phase, may be applied with a hydrophobic treatment or a portion of the inner wall surface of the groove, which is in contact with the aqueous liquid phase, may be applied with a hydrophilic treatment, or these treatments can both be applied. Moreover, when the manipulation chip is used to manipulate proteins and nucleic acids, the inner wall surface of the groove may be coated with an anti-adsorption component (such as heparin), for example, for preventing adsorption of such materials.

Further, a heating element can be disposed at the surface of the side (back side) of the substrate opposite to the side (front side) of the surface of the substrate where the groove is formed. Such substrate is applicable when the manipulation performed in the manipulation chip requires heating. The heating element can be disposed on a part of the substrate.

Specifically, in order to partially heat the manipulation medium which performs a manipulation requiring heating, the heating element can be disposed on a part of the surface of the substrate at the back side corresponding to the partial groove which accommodates the manipulation medium to be heated. More specifically, if PCR is done at the end of the manipulation in the chip, the heating element can be disposed on an end part of the surface of the substrate at the back side corresponding to a PCR solution phase in the groove.

The heating element is, for example, a metal heater, which may include platinum or the like, in particular. To dispose the metal heater on the surface of the substrate, a method of forming a metal thin film on the same can be utilized. Preferably, the metal thin film can be coated on the surface of the substrate by a sputtering method.

[2-5. Other Components]

Figure 6:
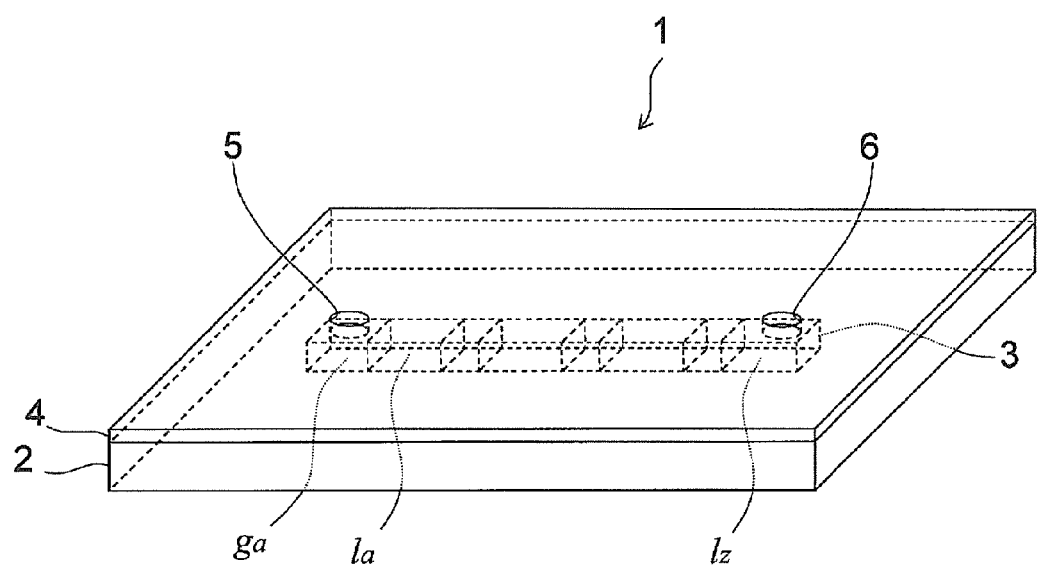
FIG. 6 shows a perspective view of an example of the manipulation chip with a cover plate disposed on a surface of the substrate.

Generally, a cover 4 is disposed on the surface of the substrate 2 at the side where the groove 3 is formed, as shown in FIG. 6. The manipulation chip 1, in which the manipulation medium is accommodated in the groove 3 of the substrate 2 and the cover 4 is disposed, is explained hereinafter. By disposing the cover 4 to cover the entirety of the groove 3 in the substrate and shield the manipulation medium accommodated in the groove 3 from an external gas, a sealed space can be formed. The material of the cover may be the same as that of the substrate, and can be selected from the viewpoint of selecting the material of the substrate. One of ordinary skill in the art can adopt an appropriate combination of the materials of the cover and the substrate, which may be the same or different, and may determine the size of the cover 4 in accordance with the size of the substrate 2 or the groove 3. For example, the size of the cover 4 is 10 to 5 mm longitudinally, 10 to 500 mm transversely, and 0.2 to 10 mm in thickness.

A hole 5 may be formed through the cover 4. The hole 5 is provided as a sample supply section for supplying the object component into the manipulation chip 1. As shown in FIG. 6, the hole 5 as the sample supply section may lead to the gel phase ga that is accommodated at one end of the groove 3. The aqueous liquid phase la, to which the object component should be supplied initially, is adjacent to the gel phase ga.

One of ordinary skill in the art may determine the size of the hole 5 in consideration of the width of the groove or the operability of the sample in this invention. The size of the hole 5 can be 0.01 to 5 mmϕ, for example.

Further, another hole 6 may be formed to penetrate the cover 4. In contrast to the hole 5 that serves as the sample supply section, the hole 6 is provided as a sample extraction section. As shown in FIG. 6, the hole 6 as the sample extraction section may lead to the aqueous liquid phase lz accommodated at the other end of the groove 3.

One of ordinary skill in the art may also determine the size of the hole 6 in consideration of the width of the groove or the operability of the sample in this invention. The size of the hole 6 can be 0.01 to 5 mmϕ, for example.

The hole 5 serving as the sample supply section and the hole 6 serving as the sample extraction section are disposed corresponding to the formation pattern of the groove. For example, one hole 5 serving as the sample supply section and one hole 6 serving as the sample extraction section may be formed in the situation of FIG. 2. In the situations shown in FIGS. 3a and 4a, one hole 5 is formed corresponding to the main groove 31 while multiple holes 6 (the number is 4 in the situations shown) are formed corresponding to a maximum branch number of the branching grooves 32. Similarly, in the situations shown in FIGS. 3b, 3c and 4b, multiple holes 5 and one hole 6 may be formed. In the situation of FIG. 5, the hole 5 and the hole 6 may both be plural.

FIG. 7 shows a modified example of FIG. 6, wherein the groove 3 having the shape of FIG. 2d is formed in the substrate 2, and the cover 4 is disposed thereon. The manipulation chip of FIG. 7 is often used in an upright manner that the wider portion of the groove is upward. The ends of the groove 3 extend to two end surfaces 71 and 72 of the substrate 2 and form openings respectively in the end surfaces 71 and 72 of the substrate 2. The hole 5 (upper hole) formed in the upper end surface 71 of the substrate 2 may serve as a sample supply section and the hole 6 (lower hole) formed in the lower end surface 72 may serve as a sample extraction section. In the example of FIG. 7, the lower hole 6 is sealed by the gel phase gz.

Figure 8:
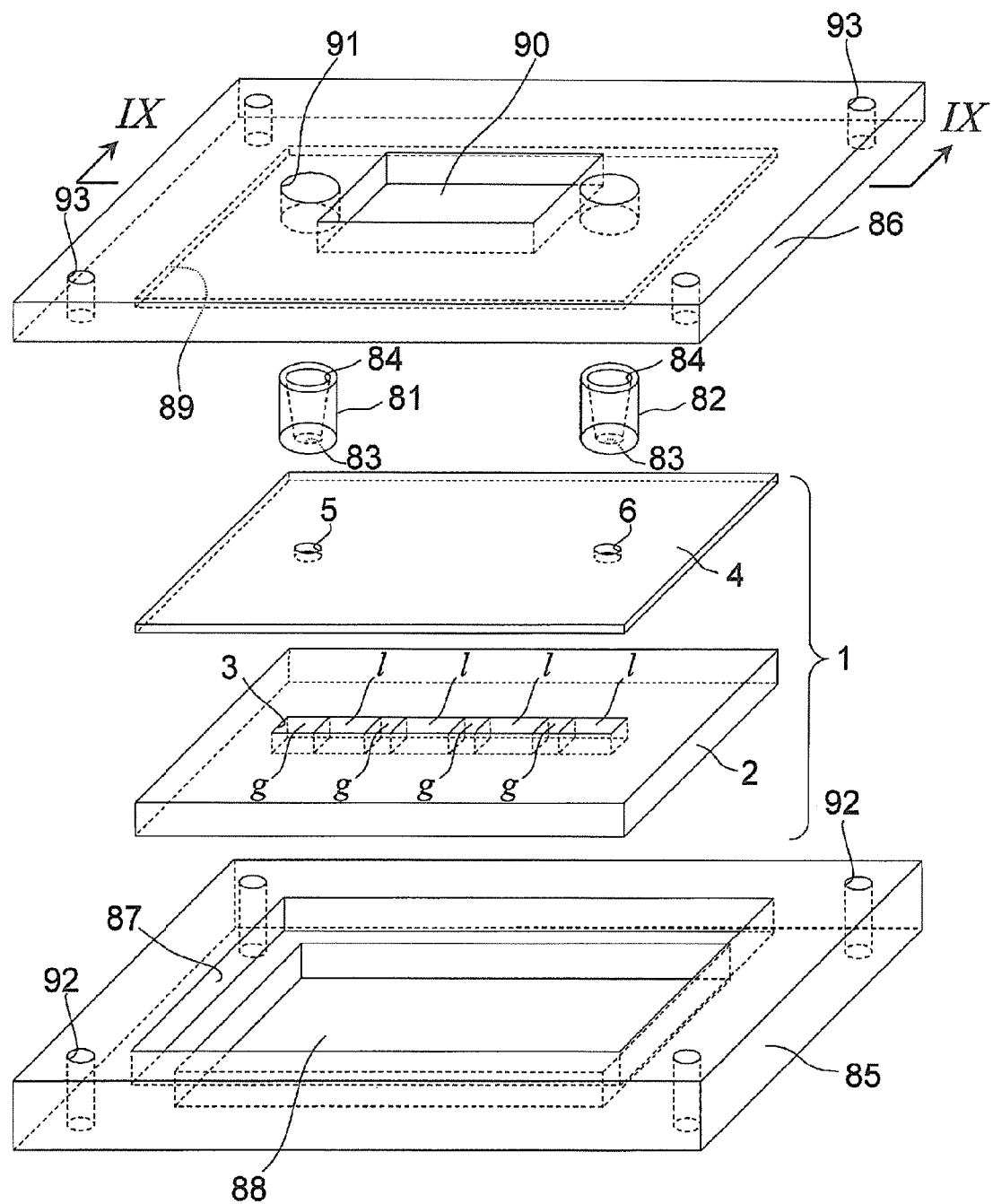
FIG. 8 shows a perspective diagram showing components of the manipulation chip of the example of FIG. 6 and the related components separately.
Figure 9:
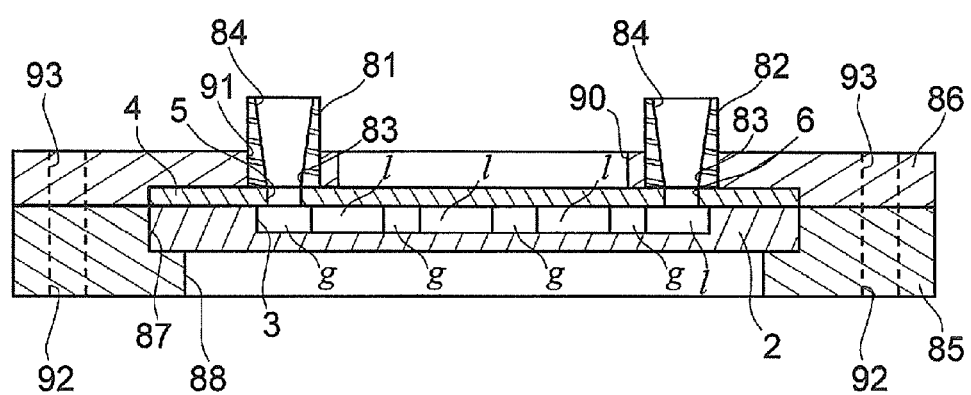
FIG. 9 shows a vertical cross-sectional view taken along the line IX-IX of FIG. 8 in a state that all the components and the related components of FIG. 8 are combined.

A more specific embodiment of the manipulation chip is explained below. FIG. 8 is a perspective diagram showing the components of the manipulation chip of FIG. 6 and related components separately. FIG. 9 shows, in a vertical cross-sectional view along line IX-IX of FIG. 8, a state that all the components in FIG. 8 are combined.

Joints 81 and 82 may be provided respectively on the holes 5 and 6. In a case that the inner diameters of the holes 5 and 6 are particularly small, the joints 81 and 82 may be disposed for the purpose of improving the operability, and the joints 81 and 82 may also store a sample solution that is to be supplied to the chip or a processed sample solution that is generated as the result of the manipulation in the chip. The joints 81 and 82 may have the same shape, which may be a substantially cylindrical member with a through hole. The through hole is formed with a diameter that preferably increases gradually from a lower opening section 83, which is formed on a lower surface of the substantially cylindrical member and corresponds to the hole 5 or 6, toward an upper opening section 84 formed on an upper surface of the substantially cylindrical member. The lower opening section 83 communicates with the hole 5 or 6, and an inner diameter of the lower opening section 83 is the same as that of the hole 5 or 6, or preferably smaller. The joints 81 and 82 can be respectively secured to the cover 4 by means of welding, adhesive, or fastening members (by screws for example; screws are not shown). If fastening members are used to secure the joints 81 and 82, a sealing material (such as O ring or packing; not shown) is disposed between the lower opening sections 83 of the joints 81 and 82 and the holes 5 and 6 of the cover 4 respectively to prevent leakage.

Considering the issue of contamination in the groove 3, it is preferred that the holes 5 and 6 are closable. For example, the entire hole or a part of the hole can be closed but remain openable. In addition, when the joints 81 and 82 are disposed on the holes 5 and 6, the entire upper opening section 84 of the joint or a part of the same may be closed but remain openable. One of ordinary skill in the art may determine a proper closable mechanism. For example, a septum (not shown) having a check valve feature, or an elastic material or gel such as PDMS may be used to partially close the hole (or the upper opening section) in an openable manner. In that case, the sample solution can be supplied or extracted by making a puncture with an injection needle. When the hole (or the upper opening section) is closed with the septum, a pressure adjustment port (not shown) may be disposed separately to adjust the pressure. The pressure adjustment port has a filter and can prevent contamination while releasing a gas equal to the amount of the injected liquid to the outside of the manipulation chip.

The substrate 2 can be fixed by a lower fixing support unit 85 and an upper fixing support unit 86. The material of the lower fixing support unit 85 and the upper fixing support unit 86 is not particularly limited, which may be a resin or metal as appropriate. Generally, the material is stronger than the substrate 2 or the cover 4.

Disposing the lower fixing support unit 85 on the lower surface of the substrate 2 can secure the side including the substrate 2 of the manipulation chip 1. On an upper surface of the lower fixing support unit 85, a fixing groove 87 is formed fitting the substrate 2. Preferably, a lower window hole 88 may be formed in the fixing groove 87, passing through and hollowing the lower fixing support unit 85. Furthermore, a plurality of screw holes 92 may be formed in the lower fixing support unit 85.

The upper fixing support unit 86 can secure the side including the cover 4 of the manipulation chip 1. On a lower surface of the upper fixing support unit 86, a fixing groove 89 is formed fitting the cover 4. Moreover, holes 91 are formed allowing the joints 81 and 82 to pass through. Preferably, an upper window hole 90 may be formed in the fixing groove 89, passing through and hollowing the upper fixing support unit 86. Further, screw holes 93 may be formed in the upper fixing support unit 86 at positions corresponding to the screw holes 92 of the lower fixing support unit 85.

The lower fixing support unit 85 and upper fixing support unit 86 are fastened to each other by a fastening member (not shown). As an example of use of the fastening member, a screw rod can be inserted into the screw hole 92 and the corresponding screw hole 93, and then a nut is screwed and fixed to the inserted screw rod. One of ordinary skilled in the art may select a proper fastening member other than the screw rod and nut.

[3. Manipulation Medium]

The number and type of the gel phase and the aqueous liquid phase that constitute the manipulation medium accommodated in the groove 3 of the substrate 2 are not particularly limited and may be determined by one of ordinary skill in the art as appropriate based on the number and type of the manipulation processes of supplying the object component.

In the manipulation medium accommodated in one groove or one branching groove, preferably, the multiple aqueous liquid phases are respectively composed of different types of aqueous liquids. The aqueous liquids that constitute the respective phases can be liquids that create the environments that are necessary for the respective treatments or reactions for the object component, used in a sequence from the side of the aqueous liquid phase la that is to be initially supplied with the object component.

In the manipulation medium accommodated in one groove or one branching groove, the multiple gel phases may be composed of the same gel, or a part of the gel phases may be composed of different gels. For example, when performing a treatment or reaction by heating in a part of the multiple aqueous liquid phases, a gel that has a high sol-gel transition point and maintains a gel state or a sol-gel intermediate state at the temperature required for the heating may be used only in the gel phases adjacent to said part of the aqueous liquid phases, and a gel that has a relatively low sol-gel transition point may be used in other gel phases. In addition, one of ordinary skill in the art may select gels having the suitable properties according to the properties and volume of the aqueous liquids forming the adjacent aqueous liquid phases.

If the grooves are branched, as shown in the branch examples of FIG. 3a-c or FIG. 4a-b for example, a phase 33 located at the branching point may be the aqueous liquid phase as shown in the figures or the gel phase. The aqueous liquid phase la, to which the object component is to be supplied initially, may be the aqueous liquid phase accommodated in a position closest to the end of the main groove side (FIG. 3a-b) or the aqueous liquid phase accommodated in a position closest to the end of the branching groove side (FIGS. 3b-c and 4b). The multiple branching grooves may accommodate manipulation media having the same pattern of aqueous liquid phases and gel phases (such as the relationship between the branching grooves 32) or accommodate manipulation media having different patterns (such as the relationship between the branching groove 32 and the branching groove 34).

In the situation that the grooves intersect each other in a grid pattern, such as the intersection form of FIG. 5, it is possible that the phase 51 located at an intersection point is the gel phase as shown in the figure while the other phases are aqueous liquid phase. It is also possible that the phase 51 at the intersection point is the aqueous liquid phase while the other phases are gel phases. In the intersection form, the gel phases may occupy a volume larger than what is shown in the figure, so as to secure the aqueous liquid phases preferably.

In the groove, the gel phase functions to separating the phases of the aqueous liquids at both sides in the longitudinal direction of the groove and stably securing the phases of the aqueous liquids in predetermined places in the groove. One of ordinary skill in the art may consider the width, depth, and length of the groove and the amount of the magnetic particles to be transported by the magnetic field application means to determine a suitable thickness of the gel phase to achieve the desired function. For example, the thickness may be 1 to 20 mm, and preferably 3 to 10 mm. Below this range, the gel phase may not have a sufficient strength for securing the aqueous liquid phases. Above this range, it is necessary to make the substrate much longer, which may reduce the operability, the durability of the device, and the accommodability.

The aqueous liquid phase provides an environment for the treatment or reaction for the supplied sample containing the object component. One of ordinary skill in the art may consider the width, depth and length of the groove, the amount of the object component, and the type of the treatment or reaction for the object component to determine a suitable thickness of the aqueous liquid phase, such that the amount of the aqueous liquid is sufficient to perform the desired treatment or reaction on the object component. The thickness of the aqueous liquid phase may be 0.5 mm to 30 mm, and preferably 3 mm to 10 mm, for example Below this range, the treatment or reaction for the object component may not be fully achieved. Above this range, the aqueous liquid phase usually becomes much thicker than the gel phase, and it is necessary to make the substrate much longer, which may reduce the operability, the durability of the device, and the accommodability.

On the other hand, if the gel phase is formed of a hydrogel, the hydrogel phase can not only serve as a partition between the aqueous liquids, but also provide an environment for the treatment or reaction for the sample containing the object component like the aqueous liquid phase. In that case, the thickness of the hydrogel phase may be greater than the thickness of the aqueous liquid phase.

[3-2. Type of Gel]

When contacted with the aqueous liquid phase, the gel phase includes a chemically inactive material that is insoluble or poorly soluble in the liquid forming the aqueous liquid phase. The phrase "insoluble or poorly soluble in the liquid" means that the solubility in the liquid at 25° C. is about 100 ppm or less. The chemically inactive material refers to a material not causing a chemical effect on the object component and the aqueous liquid or the hydrogel during the manipulation of the object component (namely, treatment of the object component in the aqueous liquid or the hydrogel, and transportation of the object component through the gel partition). The gel of this invention includes both organogel and hydrogel.

[3-2-1. Organogel]

Generally, organogel is obtained by adding a gelating agent to a water-insoluble or poorly water-soluble liquid material to gelate the liquid material.

[3-2-1-1. Water-insoluble or Poorly Water-soluble Liquid Material]

Oil that is in a liquid form at room temperature (20±15° C.) and has a solubility of about 100 ppm or less in water at 25° C. may be used as the water-insoluble or poorly water-soluble liquid material. For example, the oil may include one selected from the group consisting of liquid fat, ester oil, hydrocarbon oil and silicone oil, or a combination of at least two of the foregoing.

Examples of the liquid fat include linseed oil, *camellia* oil, macadamia nut oil, corn oil, mink oil, olive oil, avocado oil, sasanqua oil, castor oil, safflower oil, apricot kernel oil, cinnamon oil, jojoba oil, grape oil, sunflower oil, almond oil, rapeseed oil, sesame oil, wheat gemi oil, rice germ oil, rice bran oil, cottonseed oil, soybean oil, peanut oil, tea seed oil, evening primrose oil, egg yolk oil, liver oil, coconut oil, palm oil, and palm kernel oil, etc.

Examples of the ester oil include octanoate esters such as cetyl octanoate, laurate esters such as hexyl laurate, myristate esters such as isopropyl myristate and octyldodecyl myristate, palmitate esters such as octyl palmitate, stearate esters such as isocetyl stearate, isostearate esters such as isopropyl isostearate, isopalmitate esters such as octyl isopalmitate, oleate esters such as isodecyl oleate, adipate esters such as isopropyl adipate, sebacate esters such as ethyl sebacate, malate esters such as isostearyl malate, glycerin trioctanoate, and glycerin triisopalmitate, etc.

Examples of the hydrocarbon oil include pentadecane, hexadecane, octadecane, mineral oil, and liquid paraffin, etc. Examples of the silicone oil include dimethylpolysiloxane, methyl phenyl polysiloxane and other phenyl-containing silicone oils, and methyl hydrogen polysiloxane, etc.

[3-2-1-2. Gelating Agent]

An oil gelating agent selected from the group consisting of hydroxy fatty acid, dextrin fatty acid ester, and glycerin fatty acid ester, or a combination of at least two of the foregoing may be used as the gelating agent.

The hydroxy fatty acid is not particularly limited as long as it is a fatty acid with a hydroxyl group. Specific examples of the hydroxy fatty acid are hydroxymyristic acid, hydroxy palmitic acid, dihydroxy palmitic acid, hydroxy stearic acid, dihydroxy stearic acid, hydroxy margaric acid, ricinoleic acid, ricinelaidic acid and linolenic acid, etc. In particular, hydroxystearic acid, dihydroxystearic acid and ricinoleic acid are preferred among the foregoing. These hydroxy fatty acids may be used alone or in combination of two or more. Further, an animal and vegetable oil fatty acid (e.g. castor oil fatty acid, hydrogenated castor oil fatty acid, etc.), which is a mixture of the foregoing, can also be used as the hydroxy fatty acid.

Examples of the dextrin fatty acid ester include dextrin myristate [trade name "Rheopearl MKL," produced by Chiba Flour Milling Co., Ltd.], dextrin palmitate [trade name "Rheopearl KL" and "Rheopearl TL," both produced by Chiba Flour Milling Co., Ltd.], dextrin (palmitate/2-ethylhexanoate) [trade name "Rheopearl TT," produced by Chiba flour Milling Co., Ltd.] and the like, etc.

Examples of the glycerin fatty acid ester include glyceryl behenate, glyceryl octastearate, and glyceryl eicosanoate, etc. More than one of the foregoing may be used in combination, which specifically may be, e.g., TAISET26 (trade name; by Taiyo Kagaku Co., Ltd.) that contains 20% of glyceryl behenate, 20% of glyceryl octastearate and 60% of hydrogenated palm oil, or TAISET 50 (trade name; by Taiyo Kagaku Co., Ltd.) that contains 50% of glyceryl behenate and 50% of glyceryl octastearate.

The content of the gelating agent added to the water-insoluble or poorly water-soluble liquid material is 0.1 to 0.5 wt %, 0.5 to 2 wt % or 1 to 5 wt % of the total weight of the liquid material, but this invention is not limited thereto. One of ordinary skill in the art may determine the appropriate amount to achieve the desired gel and sol state.

One of ordinary skill in the art can determine an appropriate gelating method. Specifically, after heating the water-insoluble or poorly water-soluble liquid material, adding the gelating agent to the heated liquid material and completely dissolving the gelating agent, the liquid material can be gelated by cooling. An appropriate heating temperature may be determined in consideration of the physical properties of the liquid material and the used gelating agent, which is for example about 60 to 70° C. preferably. The gelating agent is dissolved in the liquid material in the heated state, and preferably the gelating agent is gently mixed when being dissolved. It is preferred to perform the cooling slowly. For example, the cooling may take about 1 to 2 hours. The cooling can be completed when the temperature drops to room temperature (15±20° C.) or lower, or preferably 4° C. or lower, for example. In an embodiment to which a preferred embodiment of the above gelating method is applied, the aforementioned TAISET 26 (produced by Taiyo Kagaku Co., Ltd.) is used, for example.

[3-2-2. Hydrogel]

The hydrogel may be prepared by using gelatin, collagen, starch, pectin, hyaluronic acid, chitin, chitosan, alginic acid, or a derivative thereof as a hydrogel material and equilibrium swelling the hydrogel material in water or an aqueous liquid, for example. Among the hydrogels described above, it is preferred to use the hydrogel prepared from gelatin. Further, the hydrogel may also be obtained by chemically crosslinking the hydrogel material described above, or processing the hydrogel material with a gelating agent (e.g. salts of alkali metals and alkaline earth metals such as lithium, potassium, magnesium, etc., salts of transition metals such as titanium, gold, silver, platinum, etc., or silica, carbon, alumina compounds, etc.). The chemical crosslinker and the gelating agent can be easily selected by one of ordinary skill in the art.

In particular, in case that the hydrogel provides the environment for the treatment or reaction for the sample containing the object component as in the case of the aqueous liquid, one of ordinary skill in the art may prepare the hydrogel appropriately such that the hydrogel has a composition suitable for the treatment or reaction.

For example, the hydrogel may be a DNA hydrogel (P-gel) with polydimethylsiloxane as a base, which is capable of synthesizing a proteins. This hydrogel includes a DNA as a part of the gel scaffold. In a case that the object component is a substrate for protein synthesis, such a hydrogel may be subjected to the reaction of obtaining the protein from the object component (which can be determined by one of ordinary skill in the art as appropriate with reference to Nature Materials 8, 432-437 (2009), and Nature Protocols 4: 1759-1770 (2009) in a more specific embodiment). The produced protein can be recovered for example by using magnetic particles having thereon an antibody specific to the protein.

[3-2-3. Properties of Gel]

The partition formed by the gel phase sandwiches the aqueous liquid in the groove on both sides in the longitudinal direction of the groove and makes it possible to secure the aqueous liquid in the predetermined place in the groove. Therefore, a state that the manipulation chip is loaded with liquid reagents in advance can be maintained from the time of manufacture till the manipulation chip is delivered to the user's hand, and the liquid reagents can be supplied stably.

On the other hand, the magnetic particles can be moved in the gel by manipulating a magnetic field from the outside, and the magnetic particles can pass through the gel, which depend on thixotropic properties (thixotropy) of the gel. That is, by moving an external magnet, the magnetic particles in the groove have a shear force to cut through the gel along the conveying surface, and the gel ahead of the traveling direction of the magnetic particles is solated and fluidized. Thus, the magnetic particles proceed in this way. After the magnetic particles pass, however, the sol released from the shear force returns to the gel state immediately, and a through-hole that the magnetic particles pass is not formed in the gel. By using this phenomenon, the object can be easily moved with the magnetic particles as carriers, and therefore the object can be switched between various chemical environments to which the object is subjected in a very short period time. For example, by applying this invention to a system including plural chemical reactions using plural reagents, the processing time of the object can be much reduced.

In addition, since it is not required to fractionate the reagents and perform a dispensing operation for each process, labor and time can be reduced, and further, deterioration of the analysis accuracy due to contamination can be prevented.

Regarding the physical properties of the gel, the storage viscoelasticity E' among the dynamic viscoelasticities is preferably 10 to 100 kPa at room temperature (20±15° C.), and more preferably 20 to 50 kPa. Below the above range, the gel partition tends to lack strength. Above this range, movement of the magnetic particles may be hindered even though the magnetic particles have a particle diameter of μms.

[3-3. Type of Aqueous Liquid]

The aqueous liquid of this invention may be any aqueous liquid that is insoluble or poorly soluble in the gel, and may be provided in the form of water, an aqueous solution, an emulsion solution called emulsion, or a suspension solution with particles dispersed therein. Regarding the components of the aqueous liquid, the aqueous liquid further includes any components for providing the environment of the reaction or treatment that the object component of this invention is subjected to.

More specifically, examples of the aqueous liquid include a solution for releasing the component as the manipulation object of this invention into the aqueous liquid phase and binding or adsorbing the component on the surfaces of the magnetic particles (specifically, a liquid with an effect of pulling the object component away from impurities and facilitating binding or adsorbing on the surface of a magnetic bead), a cleaning solution for removing impurities coexisting with the object component, an eluting solution for separating the object component adsorbed on the magnetic particles from the magnetic particles, and a reaction solution for constructing a reaction system to which the object component is provided, etc. If the object component is a nucleic acid, the aqueous liquid may be, for example, a reagent solution (cell lysis solution) for destroying a cell, releasing the nucleic acid, and adsorbing the same on the surfaces of the magnetic particles coated with silica, a cleaning solution for washing the magnetic particles to remove components other than the nucleic acid, an eluting solution (nucleic acid eluting solution) for separating the nucleic acid from the magnetic particles, or a nucleic acid amplification reaction solution for performing a nucleic acid amplification reaction, etc. A case where the object component is a nucleic acid is taken as an example below, and a treatment solution and a reaction solution for the above nucleic acid and the treatment and reaction thereof are further describes.

[3-3-1. Cell Lysis Solution]

The cell lysis solution may be a buffer solution containing a chaotropic material, for example. The buffer solution may further contain EDTA or any other chelating agent, or TritonX-100 or any other surfactant. The buffer solution is for example based on Tris-HCl or any other buffering agent. Examples of the chaotropic material include guanidine hydrochloride, guanidine isocyanate, potassium iodide, and urea, etc.

The chaotropic material is a strong protein denaturant and has the effect of pulling a protein, such as histone surrounding the nucleic acid, away from the nucleic acid and facilitating the adsorption on the surfaces of the magnetic particles coated with silica. The buffering agent can be used as an adjuvant for preparing a pH environment that facilitates the adsorption of the nucleic acid on surfaces of the magnetic particles.

The chaotropic material also has an effect of cytolysis (i.e., destroying the cell membrane). However, in terms of cytolysis (i.e., destroying the cell membrane), the surfactant contributes more than the chaotropic material.

The chelating agent can be used as an adjuvant to facilitate cytolysis.

One of ordinary skill in the art may determine a specific protocol as appropriate for extracting the nucleic acid from the sample containing the nucleic acid. In this invention, since the magnetic particles are used for transporting the nucleic acid in the droplet enclosing medium, it is preferred to utilize a method that uses the magnetic particles as the nucleic acid extraction method. For example, methods of extracting and purifying the nucleic acid from the sample containing the nucleic acid with use of the magnetic particles may be carried out with reference to Japanese Patent Publication No. 2-289596.

[3-3-2. Cleaning Solution]

Preferably, the cleaning solution is a solution that can dissolve components (e.g. proteins, sugars, etc.), other than the nucleic acid, included in the sample containing the nucleic acid, or other components in addition to the reagent used in other treatments that are performed in advance, such as nucleic acid extraction, etc., while the nucleic acid remains adsorbed on the surfaces of the magnetic particles. Specifically, the cleaning solution may include a high salt concentration aqueous solution of sodium chloride, potassium chloride or ammonium sulfate, etc., or an alcohol aqueous solution of ethanol or isopropanol, etc.

Cleaning of the nucleic acid refers to cleaning the magnetic particles on which the nucleic acid is adsorbed. A specific protocol of the cleaning may be determined by one of ordinary skill in the art as appropriate. Moreover, one of ordinary skill in the art may decide appropriate times of cleaning to clean the magnetic particles with the nucleic acid adsorbed thereon to an extent that does not cause an undesired hindrance during the nucleic acid amplification reaction. Further, from the same viewpoint, if the influence of undesired hindrance can be ignored, the cleaning process may be omitted.

The number of the aqueous liquid phases including the cleaning solution is at least equal to the number of times of cleaning.

[3-3-3. Nucleic Acid Eluting Solution]

A buffer solution containing water or salt, etc. can be used as the nucleic acid eluting solution. Specifically, a tris buffer solution, a phosphate buffer solution, and distilled water, etc. may be used.

One of ordinary skill in the art may determine a specific method as appropriate for separating the nucleic acid from the magnetic particles on which the nucleic acid is adsorbed and eluting the nucleic acid into the eluate.

[3-3-4. Nucleic Acid Amplification Reaction Solution]

The nucleic acid amplification reaction solution of this invention at least includes the nucleic acid that contains a nucleotide sequence to be amplified and the magnetic particles with the nucleic acid adsorbed on the surfaces thereof, among various elements commonly used for the nucleic acid amplification reaction.

For the nucleic acid amplification reaction as described below is not particularly limited, one of ordinary skill in the art may determine the various elements used in the nucleic acid amplification reaction as appropriate, based on a common nucleic acid amplification method described later as an example. The various elements generally include salts such as $MgCl_2$, KCl, etc., primers, deoxyribonucleotides, nucleic acid synthase, and a pH buffer solution. In addition, the above salts may be changed to other salts for use as appropriate. Further, a material for reducing nonspecific priming, such as dimethyl sulfoxide, betaine or glycerol, etc., may also be added.

In addition to the above components, it is possible to include a blocking agent in the nucleic acid amplification reaction solution of this invention. The blocking agent may be used to avoid deactivation of a nucleic acid polymerase due to adsorption on an inner wall of a reaction vessel or the surfaces of the magnetic particles, etc.

Specific examples of the blocking agent include bovine serum albumin (i.e., BSA) and other albumins, gelatin (i.e., denatured collagen), proteins such as casein and polylysine, peptide (regardless of being natural or being synthetic), ficoll, polyvinylpyrrolidone, and polyethylene glycol, etc.

The nucleic acid amplification reaction in this invention is not particularly limited, which can be a PCR method (the specifications of U.S. Pat. Nos. 4,683,195, 4,683,202, 4,800,159 and 4,965,188), an LCR method (U.S. Pat. No. 5,494,810), a Qβ method (U.S. Pat. No. 4,786,600), an NASBA method (U.S. Pat. No. 5,409,818), an LAMP method (U.S. Pat. No. 3,313,358), a SDA method (U.S. Pat. No. 5,455,166), a RCA method (U.S. Pat. No. 5,354,688), an ICAN method (Japanese Patent No. 3433929), or a TAS method (Japanese Patent No. 2843586), etc.

In addition, a RT reaction can be performed prior to the above reaction.

One of ordinary skill in the art may determine a composition of the reaction solution necessary for these nucleic acid amplification reactions, and a reaction temperature as appropriate.

In a real-time nucleic acid amplification method, it is possible to perform fluorescence detection on an amplification product by means of a fluorescent dye that can be bound to double-stranded DNA or a probe labeled with a fluorescent dye.

A detection method in the real-time nucleic acid amplification method is exemplified as follows.

For example, in a case of amplifying only an intended target by a highly specific primer, an intercalator method using SYBR™ GREEN I or the like is used.

An intercalator, which emits fluorescence through binding to double-stranded DNA, is bound to the double-stranded DNA synthesized by the nucleic acid amplification reaction and emits fluorescence of a specific wavelength on irradiation of an excitation light. By detecting the fluorescence, the amount of the amplification product can be monitored. This method does not require design and synthesis of a fluorescence labeled probe specific for the target, and can be used to measure different targets easily.

Moreover, if it is needed to detect and distinguish very similar sequences, or if typing of SNPs is performed, a fluorescence-labeled probe method is used. One example is the TaqMan™ probe method, in which an oligonucleotide with its 5' end modified with a fluorescent material and its 3' end modified with a quencher material is used as a probe.

A TaqMan probe specifically hybridizes with a template DNA in an annealing step. However, because a quencher is present on the probe, fluorescence emission is suppressed even when the probe is irradiated with excitation light. In an extension reaction step, due to the 5'→3' exonuclease activity possessed by the TaqDNA polymerase, when the TaqMan probe hybridized with the template is decomposed, the fluorescent dye is released from the probe, and the suppression of the quencher is released and fluorescence emits. The amount of the amplification product can be monitored by measuring the fluorescence intensity.

Based on such a method, a principle of determining the quantity of DNA by real-time PCR is described below. First, PCR is performed using a standard sample of a known concentration that has been serially diluted as a template. Then, the number of cycles (threshold cycle; Ct value) for reaching a certain amount of amplification product is obtained. With the Ct value as the horizontal axis, a calibration curve is made by plotting the initial DNA amount on the vertical axis.

Even for a sample with an unknown concentration, the PCR reaction is performed under the same conditions to determine the Ct value. Based on this value and the above calibration curve, the target DNA amount in the sample can be measured.

Further, in the intercalator method, by gradually raising the temperature of the liquid after the PCR reaction, which contains the fluorescent dye, from 40° C. to about 95° C. and continuously monitoring the fluorescence intensity, a melting curve of the amplification product can be obtained.

The double-stranded DNA generated by the nucleic acid amplification reaction has the length of the DNA and a Tm value that is inherent in the nucleotide sequence. That is, as the temperature of the droplet that contains the DNA bound with the fluorescent dye is gradually increased, the temperature at which the fluorescence intensity decreases drastically is observed. When the change in fluorescence intensity is examined, a temperature peak is substantially coincident with the nucleotide sequence and the Tm value defined by the length. Thereby, it is possible to exclude the data (i.e., false positive data) observed due to generation of, for example, a primer dimer, instead of the target gene, from the data considered positive. In genetic testing, impurities in the sample often cause a non-specific reaction, so eliminating such false positives is important. Thus, whether the generated amplification product is inherent in the target gene can be determined.

[3-3-5. Other Aqueous Liquid]

One of ordinary skill in the art can also easily determine the composition of each aqueous liquid for any reaction and treatment other than the aforementioned. Moreover, even if the object component is not the nucleic acid described above, one of ordinary skill in the art can easily determine the composition of each aqueous liquid.

[4. Manufacturing Method of Manipulation Chip]

Figure 10:
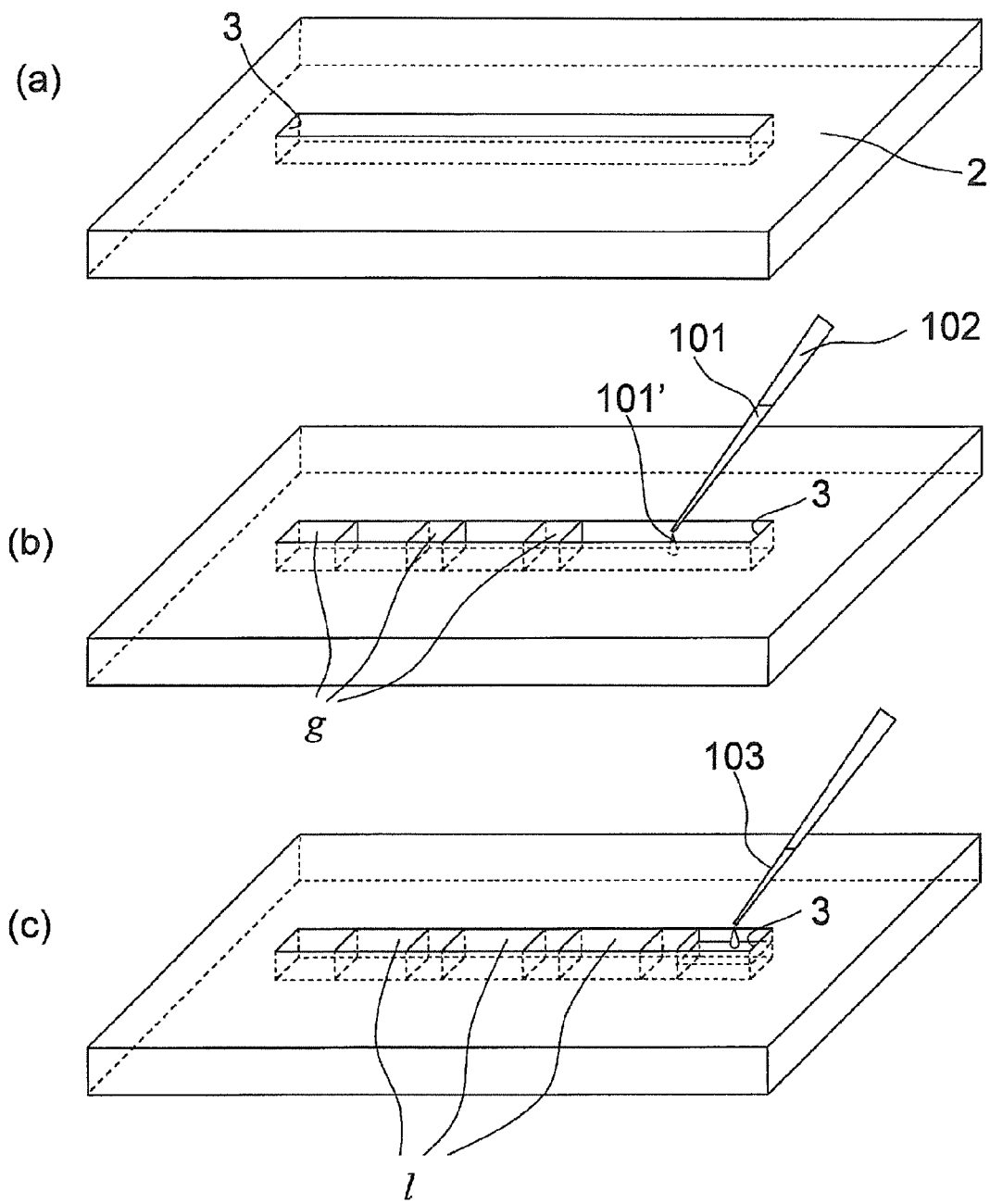
FIG. 10 schematically shows, in a perspective view, an example of a method for manufacturing the manipulation chip.

A method for manufacturing the manipulation chip is explained with reference to the example of FIG. 10.

First, a groove 3 is formed in a surface of a substrate 2 (FIG. 10*a*). One of ordinary skill in the art may carry out the formation of the groove 3 as appropriate. For example, a technique used in the field of MEMS (Micro Electro Mechanical System) may be applied to form the groove 3. For example, in a case where the material of the substrate is glass, an etching technique or a sand blasting technique may be used to form the groove. Moreover, in a case where the material of the substrate is a resin, the groove may be formed using a cutting process or a mold in addition to the above exemplified techniques used for glass.

After the groove 3 is formed, a hydrophobic treatment may be performed on a surface of the groove 3 where a gel phase is to be disposed (that is, the groove surface to be in contact with the gel phase when a manipulation medium is accommodated therein). Further, a hydrophilic treatment may be performed on another surface of the groove 3 where an aqueous liquid phase is to be disposed (that is, the groove surface to be in contact with the aqueous liquid phase when the manipulation medium is accommodated therein). In addition, the hydrophobic treatment and the hydrophilic treatment may both be performed. One of ordinary skill in the art may select an appropriate common surface treatment to carry out the hydrophobic treatment or the hydrophilic treatment. If the material of the substrate is glass or quartz, the hydrophobic treatment may be performed using a silylation agent or the like, for example. The hydrophilic treatment may be a plasma treatment, for example.

Besides, the surface of the groove 3 may be coated with a material (e.g., heparin) for preventing adsorption of a biological material, such as a nucleic acid or a protein.

In the groove 3 formed in the substrate 2, it is possible to form the gel phase section of the manipulation medium first and then form the aqueous liquid phase section. When the gel phase section is formed, a plurality of gel blocks are arranged in separated states in the longitudinal direction of the groove 3.

In a specific example of the method for forming the gel phase section, a plurality of locations in the groove 3 may be stuffed with gel blocks that are already in a gel state.

In another specific example (FIG. 10*b*) of the method for forming the gel phase section, a sol material 101 prepared in a sol state by heating a gel material over a gel-sol transition point may be disposed at a plurality of locations in the groove 3 by dripping the sol material 101 through a suitable dripping means 102. If it is difficult for drips 101' to enter the groove, the substrate may be placed in a depressurization chamber to perform the process under depressurization.

Generally, the sol material 101 is in a heated state. While the sol drips 101' are released from the dripping means 102, or after the sol drips 101' are released from the dripping means 102, usually the sol drips 101' are away from a heat source to an extent that the sol drips 101' are in an intermediate state that has high viscoelasticity due to incomplete gelation.

Due to the viscoelasticity, the gel-sol intermediate material does not spread like a liquid in the groove 3, but instead remains like a block at the predetermined location. Thus, when the hydrophobic treatment is performed on the surface of the groove 3 where the gel phase is to be disposed and/or when the hydrophilic treatment is performed on the surface of the groove 3 where the aqueous liquid phase is to be disposed, for example, the gel-sol intermediate material can remain like a block at the predetermined location more stably.

Then, by further cooling the gel-sol intermediate material to completely gelate the gel-sol intermediate material, a gel block g (i.e., gel phase section) is formed.

Next, an aqueous liquid 103 is disposed to fill the groove space adjacent to the gel phase section g, so as to complete the aqueous liquid phase section 1 (FIG. 10*c*). If it is difficult for the aqueous liquid 103 to enter the groove, the substrate may be placed in a depressurization chamber to perform the process under depressurization.

After completing the gel phase section g and the aqueous liquid phase section 1, a cover 4 can be disposed on the surface of the substrate 2 at the side where the groove 3 is formed. A hole 5 and a hole 6 may be formed in advance to penetrate the cover 4 at positions corresponding to the end portions of the groove 3 (more specifically, to communicate with the phases accommodated at the ends of the groove 3 when the cover 4 is bonded to the substrate 2). Moreover, when the cover 4 is bonded to the substrate 2, the hydrophobic treatment may be performed on a surface of the cover 4 that is to be in contact with the gel phase accommodated in the groove, or the hydrophilic treatment may be performed on another surface of the cover 4 that is to be in contact with the aqueous liquid phase, or both treatments may be performed. If the manipulation chip is used for manipulating samples such as a protein or a nucleic acid, etc., the surface may be coated with an adsorption preventing component (e.g., heparin) so as to prevent adsorption of the samples.

The substrate 2 and the cover 4 are bonded to each other with the groove 3 inside.

The method of bonding the substrate 2 and the cover 4 may be a bonding method with addition of energy, such as a heat fusion method, an ultrasonic fusion method or a pressure bonding method (laminate-sealing method), etc., or a bonding method with use of an adhesive agent or a filler agent, for example. Since the aqueous liquid is accommodated in the substrate 2, it is preferred to carry out the bonding under a mild condition. In the case that the adhesive agent is used, a variety of adhesive agents may be used, such as epoxy adhesives, isocyanurate-based adhesives, vinyl acetate adhesives, nitrocellulose adhesives, cyanoacrylate adhesives, and silicone adhesives, etc.

One of ordinary skill in the art may select an appropriate adhesive agent that has high water resistance and causes less influence to the reaction in the substrate. In addition, a sol material similar to the above sol material 101 may be used as an adhesive agent for adhesion through gelation. Particularly, if a material capable of occluding gas is used to form the substrate 2 and/or the cover 4, the substrate 2 with the cover 4 thereon may be placed in a depressurization environment for the material to occlude gas that may remain in the groove 3 so as to remove the gas.

Furthermore, a method that places the cover 4 on the substrate 2 and crimps with a jig to fix the cover 4 may be an alternative for bonding the substrate 2 and the cover 4. Considering the crimping properties between the two members, this method is used preferably for a case that the substrate 2 and/or the cover 4 is made of an elastic material (e.g. polydimethylsiloxane).

In particular, if the manipulation chip 1 formed by bonding the substrate 2 and the cover 4 includes a member made of a fragile material such as glass, a packing made of an elastic material (e.g. silicone rubber) is disposed on an upper surface (the surface at the side of the cover 4) and/or a lower surface (the surface at the side of the substrate 2), and the related members as shown in FIG. 8 and FIG. 9 may be attached thereto. Specifically, the manipulation chip 1 may be sandwiched between a lower fixing support unit 85 and an upper fixing support unit 86 and held by fastening the two support units to each other with use of a fastening member.

A joint 81 and a joint 82 may be respectively fixed to the upper surface (the surface at the side of the cover 4) of the manipulation chip 1 through adhesion or welding, or may be fastened to the upper surface (the surface at the side of the cover 4) of the manipulation chip 1 using the fastening member with a seal material disposed between the joints 81 and 82 and the holes 5 and 6. Accordingly, the lower opening sections 83 of the joints 81 and 82 are in communication with the holes 5 and 6 respectively. The upper opening sections 84 can be closed appropriately with a septum, etc.

[5. Magnetic Particle]

The magnetic particles are adapted to move together with the object component in the manipulation chip in response to a variation of a magnetic field outside the manipulation chip. The magnetic particles that achieve separation, recovery, and purification of the object component by such movement usually have a chemical functional group on the surfaces thereof. The magnetic particles may or may not be accommodated in the manipulation chip in advance. If the magnetic particles are accommodated in the manipulation chip in advance, the magnetic particles may be contained in the aqueous liquid phase 1a that is to be supplied with the object component initially. If the magnetic particles are not accommodated in the manipulation chip in advance, when supplying the sample containing the object component to the chip, the magnetic particles may be mixed into the sample to be supplied to the chip.

The magnetic particles are not particularly limited as long as they are particles responsive to magnetism, which may be particles having a magnetic material such as magnetite, γ-iron oxide, and manganese zinc ferrite, etc. Moreover, the surfaces of the magnetic particles may have a chemical structure, such as an amino group, a carboxyl group, an epoxy group, avidin, biotin, digoxigenin, protein A, protein G, complexed metal ions, or an antibody, which specifically binds to the object component supplied for the above treatment or reaction, or the surfaces may specifically bind to the object component by electrostatic force or van der Waals force. Thus, the object component supplied for the reaction or treatment can be selectively adsorbed on the magnetic particles.

Examples of the hydrophilic group on the surfaces of the magnetic particles include a hydroxyl group, an amino group, a carboxyl group, a phosphoric acid group, and a sulfonic acid group, etc.

In addition to the above, the magnetic particles may further contain various elements which can be selected by one of ordinary skill in the art as appropriate. For example, in a specific embodiment, the magnetic particles that contain a hydrophilic group on the surfaces are preferably particles formed of a mixture of a magnetic material and a silica and/or anion exchange resin, magnetic particles having surfaces covered with silica and/or anion exchange resin, magnetic particles having surfaces covered with gold that has a hydrophilic group through a mercapto group, or gold particles having a hydrophobic group through a mercapto group on their surfaces containing a magnetic material, etc.

Regarding the size of the magnetic particles having a hydrophilic group on their surfaces, the average particle diameter may be about 0.1 μm to 500 μm. If the average particle diameter is small, the magnetic particles are likely to exist in a dispersed state in the aqueous liquid phase as the magnetic particles are released from the magnetic field.

Taking magnetic particles available in the market as an example, magnetic beads coated with silica for nucleic acid extraction, which are a constituting reagent of Plasmid DNA Purification Kit MagExtractor-Plasmid-sold by Toyobo, may be used as the magnetic particles. If the magnetic particles are sold as a constituting reagent of a kit as described above, the product stock solution containing the magnetic particles includes a preservative solution or the like. Therefore, it is preferred to wash it by suspension in pure water (e.g., about 10 times in volume). The washing may be performed by removing the supernatant simply through a centrifugal operation or agglomeration using a magnet after the suspension, or by repeating the suspension and the supernatant removal processes.

[6. Magnetic Field Application Means]

[6-1. Magnetic Field Application Means]

There is no particular limitation on the magnetic field application means and a magnetic field moving mechanism including the magnetic field application means, which cause the variation in the magnetic field for moving the magnetic particles together with the object component in the manipulation chip. A magnetic source, such as a permanent magnet (e.g., a ferrite magnet or a neodymium magnet) or an electromagnet, may be used as the magnetic field application means.

Figure 11:
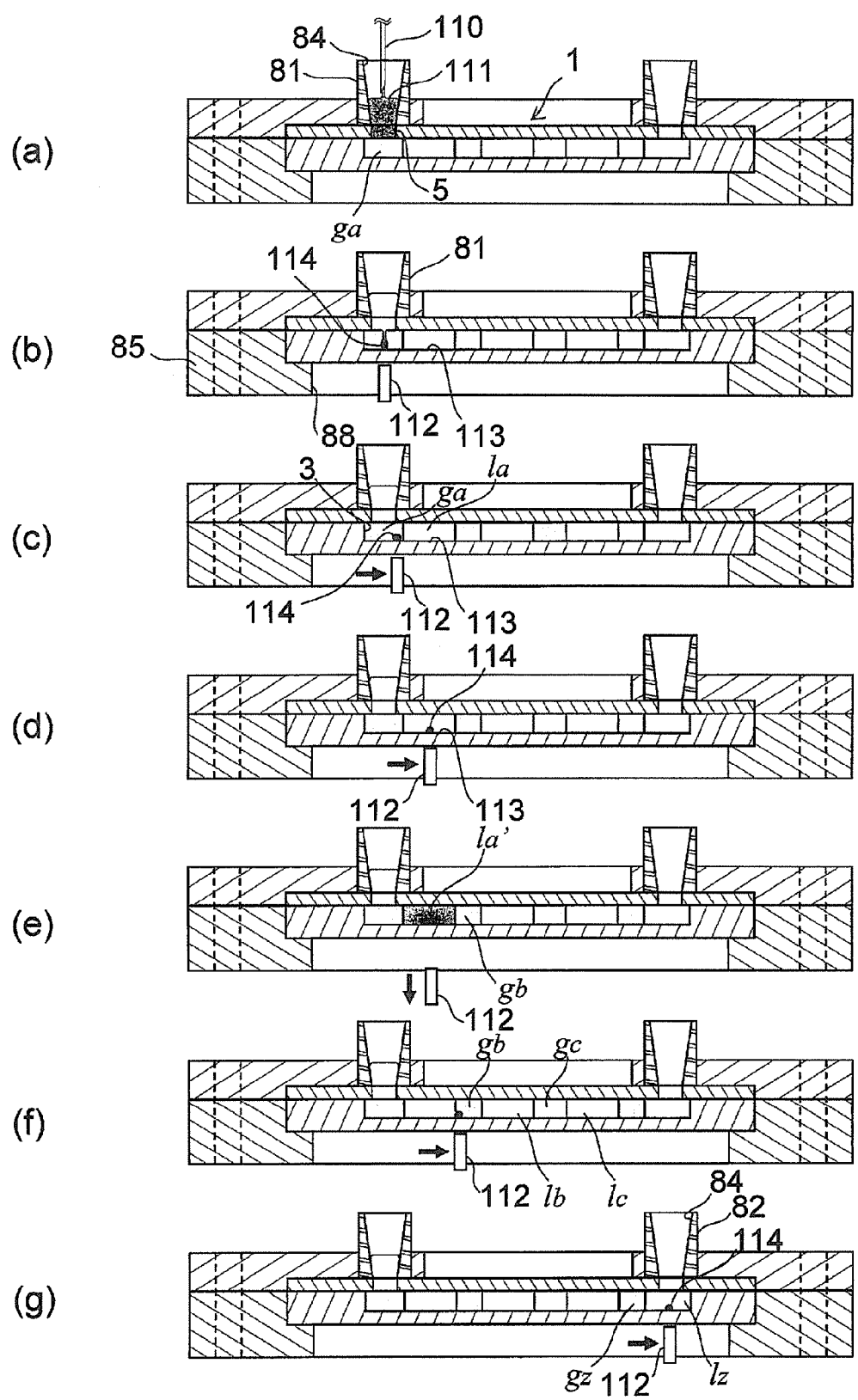
FIG. 11 schematically shows, in a vertical cross-sectional view, an example of a basic manipulation using the chip device.

Referring to FIG. 11 a-g which shows an exemplary embodiment of use of the chip device of this invention as described in Section 8 below, the magnetic field application means is disposed close to the manipulation chip 1 from the outside of the manipulation chip 1, as represented by, e.g., 112 in FIG. 11d. The magnetic field application means is close to a certain extent that the magnetic particles 114 in the aqueous liquid phase la' in the groove 3 can be aggregated to the side of the conveying surface 113. While the magnetic field application means 112 is maintained close to the manipulation chip 1 as above, the magnetic field application means 112 is moved substantially in parallel to the surface of the manipulation chip 1 in the longitudinal direction of the groove 3. Thus, as shown in FIG. 11c, the magnetic particles 114 can be aggregated to the side of the conveying surface 113 and be transported even in the gel phase ga of the manipulation chip 1. Accordingly, the magnetic field application means generates the magnetic field effective to the magnetic particles 114 through the conveying surface 113 in the groove 3 and can trap and transport the object component with the magnetic particle block.

[6-2. Magnetic Field Moving Mechanism]

[6-2-1. Movement in Longitudinal Direction of the Groove in the Manipulation Chip]

The magnetic field moving mechanism including the magnetic field application means is capable of moving the magnetic field in the longitudinal direction of the groove in the manipulation chip while the magnetic particles are maintained in the aggregated state. The magnetic field moving mechanism described below may be a mechanism capable of determining a stop position or controlling a moving speed, and the control may be performed manually or automatically by a computer, etc. For example, the moving speed may be 0.5 mm to 10 mm per second.

Preferably, the magnetic field moving mechanism is capable of causing the magnetic field application means to move itself physically in the longitudinal direction of the groove in the manipulation chip.

[6-2-2. Control of Strength of Magnetic Field]

The magnetic field moving mechanism including the magnetic field application means may be a mechanism capable of variably controlling the strength of the magnetic field applied to the magnetic particles. Specifically, the magnetic field may be blocked or reduced. Preferably, the magnetic field is blocked or reduced to an extent that can cause the magnetic particle group aggregated by the magnetic field to disperse in the aqueous liquid phase.

For example, if the magnetic field is generated by an electromagnet, the magnetic field can be blocked by using a power supply control means.

Moreover, if the magnetic field is generated by a permanent magnet as shown in FIG. 11e, for example, a mechanism can be used to move the magnet disposed outside the manipulation chip away from the manipulation chip. This mechanism may be controlled manually or automatically. When the magnetic field applied to the magnetic particles is reduced, preferably the magnetic particles are released from the magnetic field, and as a result, the magnetic particle group naturally disperses in the aqueous liquid phase. Thus, the object component adhered to the magnetic particles and other unnecessary components that may accompany the object component can be sufficiently exposed to the liquid that makes up the aqueous liquid phase.

[6-2-3. Case where Multiple Manipulation Chips are Clustered in the Device]

Figure 13:
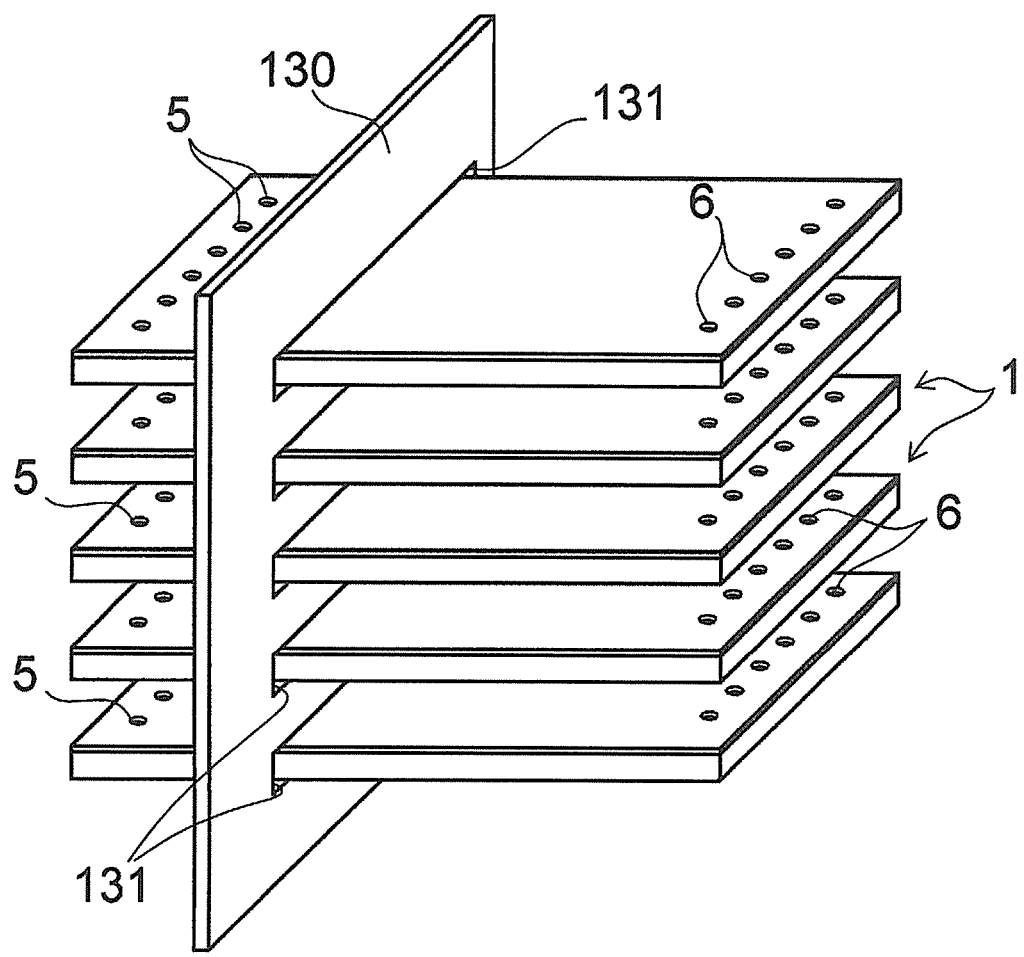
FIG. 13 shows a perspective view of an example of an integrated chip device including a plurality of manipulation chips.
Figure 14:
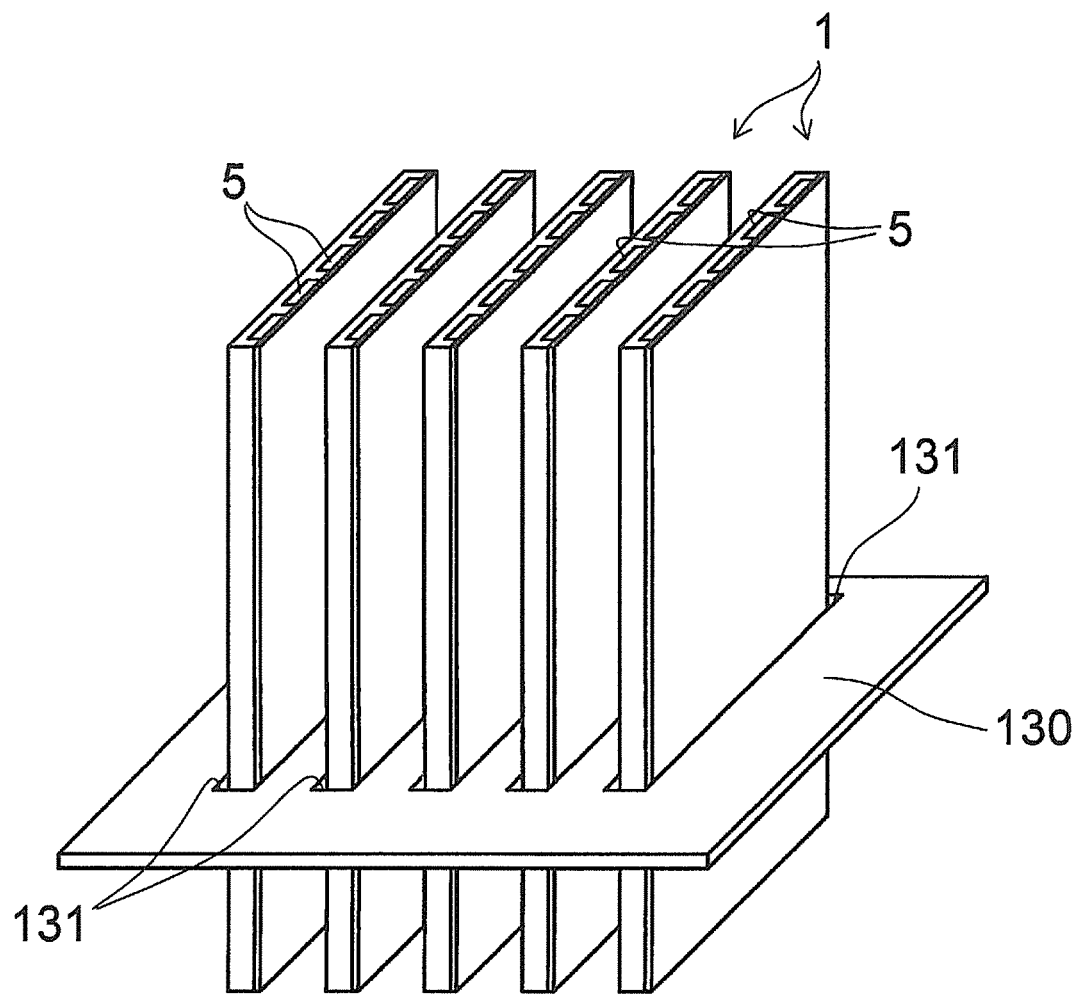
FIG. 14 shows a perspective view of another example of the integrated chip device including a plurality of manipulation chips.

FIG. 13 shows an example of an integrated device with a plurality of manipulation chips clustered therein. Each manipulation chip 1 of FIG. 13 is a modified example of that of FIG. 6, and has a plurality of grooves formed therein. FIG. 14 shows another example of the integrated device. Each manipulation chip 1 of FIG. 14 is a modified example of the manipulation chip of FIG. 7, and has a plurality of grooves formed therein. In the devices of FIGS. 13-14, a plurality of magnetic sources provided corresponding to the plurality of manipulation chips can be unitized to a member that is movable in the longitudinal direction of the groove in the manipulation chip so as to be held. As shown in the figures, such unitizing member may be embodied by a movable magnetic plate 130 as a magnetic field application means movable in the longitudinal direction of the groove in the manipulation chip 1. The movable magnetic plate 130 is formed with holes 131 respectively corresponding to the manipulation chips 1. By inserting the chips 1 into the holes 131 respectively, application and movement of the magnetic field can be performed on the plurality of chips 1 simultaneously.

[6-2-4. Oscillation of Magnetic Field]

The magnetic field moving mechanism may include a mechanism for achieving an oscillating movement, such as amplitude movement or rotation, of the magnetic field. The function that the magnetic source is capable of performing oscillating movement or rotational movement in the longitudinal direction of the groove in the manipulation chip can substitute for a stirrer, for example. Accordingly, it is easy to carry out mixing or stirring in the aqueous liquid.

For example, if the device does not have the function of blocking or reducing the magnetic field, the magnetic field application means can perform the oscillating movement or the rotational movement several times within the range of the thickness of the aqueous liquid phase while being kept close to the manipulation chip (that is, while the magnetic particles are aggregated), so as to sufficiently expose the object component adsorbed on the magnetic particles in the aqueous liquid to the liquid that makes up the aqueous liquid phase.

[7. Optical Detection Means]

When performing a detection process in the manipulation chip by optical analysis, there is no particular limitation on the optical means used in the process. One of ordinary skill in the art can easily select the optical means according to the analysis method for the supplied object component. For example, a means that includes a light generating unit, a detection means, a light transmission means and a personal computer, etc. as appropriate can be used.

In an example, light emitted from the light generating unit may enter the detection means (e.g., a light transmission means such as an optical fiber cable attached to a detection lens), and a reaction liquid that constitutes the aqueous liquid phase accommodated in the manipulation chip may be irradiated by the light through the detection lens. An optical signal detected by the detection lens may be transmitted to a light-receiving element through the optical fiber cable and converted to an electrical signal, and then transmitted in real time to the personal computer to monitor the change of the fluorescence intensity of the reaction liquid. This is suitable for a case of this invention that performs a reaction or treatment with detection of the fluorescence intensity that may reflect the variation of the real-time nucleic acid amplification reaction, etc.

A LED, a laser or a lamp, etc., may be used as the light generating unit. In addition, the light-receiving element is not particularly limited. Various light-receiving elements, such as an inexpensive photodiode or even a photomultiplier tube that has higher sensibility, can be used for the detection.

Taking a case of performing the nucleic acid-related reaction such as a real-time nucleic acid amplification reaction or a nucleic acid-related treatment as an example, when SYBR™ GREEN I is used, for example, the dye is specifically bound to the double-stranded DNA and produces fluorescence near 525 nm. Thereby, the detection means can cut light not of the target wavelength with an optical filter so as to detect the light of the target wavelength.

[8. Method of Manipulating Object Component with Use of Chip Device]

A basic manipulation of the object component with use of the chip device is explained below based on the example illustrated in FIG. 11a-g.

[8-1. Basic Manipulation]

In one example of use of the chip device, a sample solution 111 containing the object component is supplied using an injection needle 110 through the upper opening section 84 of the joint 81, which is closed by a sealing means (not shown) such as a septum (FIG. 11a). The sample solution 111 contains magnetic particles in a dispersed state. In the case as shown, the sample solution 111 is dammed by the initial gel phase ga and fills a part of the inside of the joint 81 and the space in the hole 5.

As a magnet 112 is moved close to the manipulation chip 1, a magnetic field is generated in the direction of the sample solution 111 accumulated in the joint 81 from the side of the conveying surface 113 (FIG. 11B). Accordingly, the magnetic particles 114 that are dispersed in the sample solution 111 can be aggregated and separated in the direction of the conveying surface 113. Because the lower fixing support unit 85 is formed with the lower window hole 88, the magnet 112 can easily approach the manipulation chip 1 to generate a sufficient magnetic force.

The group of the magnetic particles 114 aggregated by the magnetic force is thinly coated with the sample solution 111 in the gel phase la and adsorbs the object component as well as unnecessary components thereto (FIG. 11 c).

In the gel phase la, the group of the magnetic particles 114 moves on the conveying surface 113 following the magnet 112 as the magnet 112 is moved in the longitudinal direction of the groove 3. Due to the thixotropic properties (thixotropy) of the gel, the group of the magnetic particles 114 remains moving in the aforementioned state without forming a through-hole in the gel.

By moving the magnet 112 further, the group of the magnetic particles 114 is moved into the aqueous liquid phase la (FIG. 11d). Thus, in the aqueous liquid phase la, an aqueous liquid mixture la' that includes the sample containing the object component and the magnetic particles is generated.

In addition to the method illustrated above, the aqueous liquid mixture may also be prepared by disposing the magnetic particles in the aqueous liquid phase la in advance and then supplying only the sample solution into the manipulation chip. In that case, the aqueous liquid phase la is located to communicate with the hole 5.

In consideration of improving the process efficiency, in the aqueous liquid phase, it is preferred to manipulate the magnet such that the magnetic particles carrying the object component are sufficiently in contact with the aqueous liquid. Specifically, the magnet 112 may be moved away from the manipulation chip 1 to reduce the magnetic force, so as to disperse the magnetic particles 114 previously in the aggregated state to the aqueous liquid phase la (FIG. 11E).

If the liquid making up the aqueous liquid phase la is capable of releasing the nucleic acid contained in the sample solution 111 and binding or adsorbing the nucleic acid on the magnetic particles, the treatment of nucleic acid extraction can be performed by the above manipulation.

Then, the magnet 112 is moved close to the manipulation chip 1 again to generate the magnetic field and aggregate the magnetic particles 114 dispersed in the phase of the aqueous liquid mixture la'. The magnet 112 is moved further in the longitudinal direction of the groove 3 to move the magnetic particles 114 into the gel phase gb (FIG. 11f). In the gel phase gb, the aggregated magnetic particles 114 are thinly coated with a liquid component contained in the aqueous liquid mixture la'. Therefore, not only the nucleic acid that is the object component, impurities such as the unnecessary components are also carried by the magnetic particles 114.

By moving the magnet 112 further, the magnetic particles with the nucleic acid can be transported into the adjacent aqueous liquid phase lb through the gel phase gb. In the aqueous liquid phase lb, the magnet can also be manipulated to cause the magnetic particles to sufficiently contact the aqueous liquid. If the liquid making up the aqueous liquid phase lb is a cleaning solution, the treatment of nucleic acid purification can be performed by removing the impurities accompanying the nucleic acid with the above manipulation.

Similarly, the magnetic particles carrying the nucleic acid may be transported into the adjacent aqueous liquid phase lc through the gel phase gc to perform the same manipulation as in the aqueous liquid phase lc. If the liquid making up the aqueous liquid phase lc is a cleaning solution, impurities that may remain in the nucleic acid which has been purified in the above process may be further removed to improve the purity of the nucleic acid.

Moreover, with the magnet 112, the above manipulation may be repeated where necessary.

In addition to the disclosure of FIG. 11, in an example where the aforementioned manipulation is repeated, other aqueous liquid phases and gel phases exist between the aqueous liquid phases lc and lz. In such a case, the transporting manipulation and the treatment manipulation may be reiterated for a number of times corresponding to the number of the phases. In principle, the magnetic particles can be moved in only one direction from the aqueous liquid phase la to the aqueous liquid phase lz.

In another example where the above manipulation is repeated, in the manipulation chip shown in FIG. 11, it is allowed to reiterate the above process by reciprocating between the aqueous liquid phases.

Finally, the magnetic particles 114 no which the purified nucleic acid is adsorbed is transported into the aqueous liquid phase lz through the gel phase gz (FIG. 11g). In the gel phase gz, the amount of the impurity component carried by the magnetic particles and the nucleic acid is close to zero as possible. While very little cleaning solution remains on the magnetic particles, the nucleic acid on the particle surface has been purified to a level not hindering the later treatment in the aqueous liquid phase lz.

If the liquid making up the aqueous liquid phase lz is a nucleic acid amplification reaction solution, amplification of a target nucleic acid in the purified nucleic acid can be performed. The nucleic acid amplification product can be analyzed by a fluorescence detection method based on a real-time detection method or an end-point detection method using a fluorescent dye. A temperature control means or an optical detection means is not shown in FIG. 11.

After completing the treatment in the aqueous liquid phase lz, where necessary, the treatment solution can be extracted using an injection needle or the like from the upper opening section 84 of the joint 82 that is closed by a sealing means (not shown) such as a septum.

While the last phase is the aqueous liquid phase lz in the example of FIG. 11, in other examples, the last phase may be the gel phase gz. In the example that the last phase is the gel phase gz, the magnetic particles are recovered in the gel phase gz. The recovery is performed for purposes of storing the magnetic particles together with the sample processed by the manipulation and adsorbed on the magnetic particles, and analyzing the sample processed by the manipulation and adsorbed on the particles in a separate apparatus. The recovery method is specified by the following three examples.

In an example of the recovery method for recovering the magnetic particles from the last gel phase gz, a break induction groove is formed at a desired position between the members of the manipulation chip, and the chip is detached by the break induction groove, so as to recover the magnetic particles contained in each gel phase gz.

The break induction groove is formed extending in a direction substantially perpendicular to the longitudinal direction of the groove. After completing the processing in the manipulation chip 1, an external force is applied to cause breaking by the break induction groove, thereby detaching a portion of the manipulation chip as a chip piece. The detached chip piece includes the portion of the gel phase gz containing the magnetic particles as a recovered product.

In another example of the recovery method for recovering the magnetic particles from the last gel phase gz, as described below, a recovery vessel is connected to the manipulation chip so as to recover the magnetic particles into the recovery vessel using the magnetic field application means.

Figure 12:
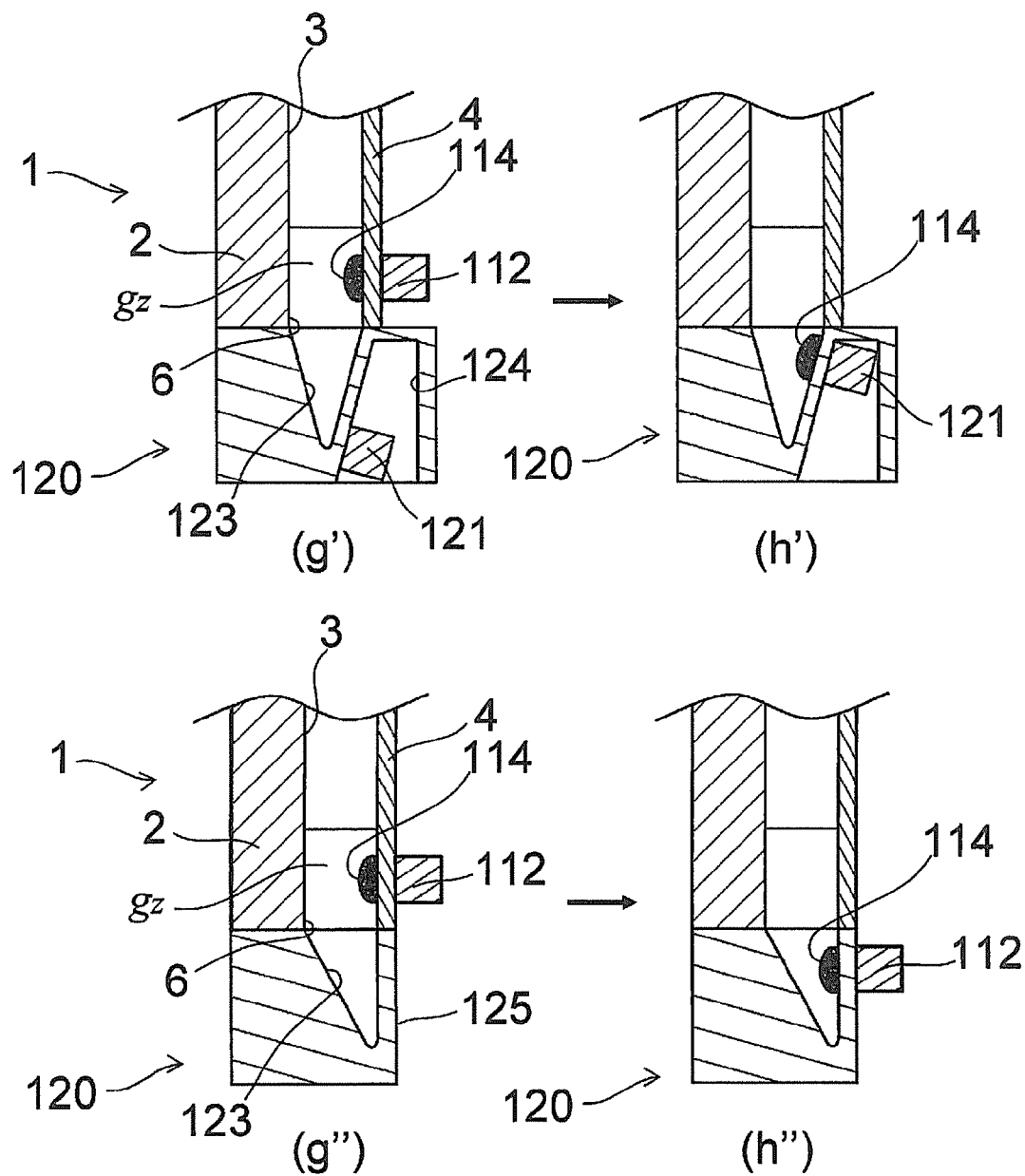
FIG. 12 schematically shows, in a (partial) vertical cross-sectional view, two examples of a method of recovering magnetic particles obtained by a manipulation using the manipulation chip of FIG. 7, wherein in the respective examples, processes g' and g" correspond to the process g of FIG. 11.

Like the manipulation chip of FIG. 7, in a case that the groove 3 extends to the surfaces at two ends of the substrate 2 and forms openings on the respective surfaces (upper hole 5 and lower hole 6), the magnetic particles can be extracted from the lower hole 6 of the surface by the method illustrated in FIG. 12 (illustrating the portion near the lower end of the manipulation chip).

FIG. 12 illustrates two examples. In the respective examples, the processes g' and g" corresponding to the process g of FIG. 11 and the subsequent processes h' and h" are illustrated by vertical cross-sectional diagrams.

In the example of FIG. 12, a recovery vessel 120 is used. As shown in the figure, the recovery vessel 120 is formed with a recovery unit 123 which is a hollow block having an opening on the top surface. In addition, as shown by the process g', a magnet through hole 124 may be formed for a recovery vessel side magnet 121, which is other than the magnet 112 used in the manipulation of the manipulation chip, to generate a magnetic field to the recovery unit 123 from the outside.

The recovery vessel 120 is connected to the lower end of the manipulation chip 1 such that the lower hole 6 on the side of the manipulation chip 1 and the upper opening end of the recovery unit 123 on the side of the recovery vessel 120 correspond to each other. The manipulation in the manipulation chip 1 is finished, and the magnetic particles 114 carrying the sample processed by the manipulation reach the gel phase gz (g'). Thereafter, the magnet 121 at the side of the recovery vessel 120 is raised, and the magnetic particles 114 are transferred from the magnet 112 to the recovery vessel side magnet 121 (h'). Accordingly, the magnetic particles 114 are recovered into the recovery vessel 120 from the inside of the manipulation chip 1.

The embodiment presented by the processes g" and h" is a modified example where the shape of the recovery vessel 120 is changed. In the recovery vessel 120 of this embodiment, the recovery unit 123 is faulted asymmetrically, and a magnet access surface 125 of the recovery vessel 120 and the surface of the cover 4, which is a magnet access surface of the manipulation chip 1, are substantially on the same plane. For this reason, the magnetic particles 114 can be recovered into the recovery vessel 120 using the magnet 112 that is used for the manipulation of the manipulation chip 1 (h").

The recovery vessel may have the shape of the hollow block shown in FIG. 12 or may be shaped like a container such as a tube. In addition, like the device shown in FIG. 14, if multiple grooves are formed in one manipulation chip, or multiple pieces of manipulation chips are integrated, which requires recovery of the magnetic particles from multiple lower holes, the recovery vessel may be a block formed with multiple holes, like a multi-hole well. Or, the recovery vessel may be embodied by connecting a plurality of containers such as tubes corresponding to the number of the lower holes.

In yet another example of the recovery method for recovering the magnetic particles from the last gel phase gz, the recovery vessel is connected to the manipulation chip and a gas pressure is utilized to move the gel phase gz, so as to recover the magnetic particles of each gel phase gz to the recovery vessel. According to the above example, the recovery vessel may have the recovery unit. However, in order to adjust the pressure, the recovery vessel further has a gas through hole communicating with the recovery unit.

For example, after connecting the recovery vessel to the manipulation chip as in the previous example, a suitable adapter is connected to the sample supply section side for applying a pressure into the groove, so as to cause all the manipulation medium to slide in the direction of the sample extraction section. The gel phase gz pops out of the sample extraction section and enters the recovery unit of the recovery vessel for performing the recovery. The recovery process can be completed by stopping applying the pressure. Alternatively, instead of applying pressure into the groove at the sample supply section side, depressurization may be performed via the gas through hole of the recovery vessel to achieve the same recovery process.

[8-2. Case where Manipulation is Performed in the Direction from One Main Groove to Multiple Branching Grooves]

If the grooves branch or intersect each other, the manipulation can be carried out with even higher efficiency.

For example, as shown in FIG. 3a or 4a, when the manipulation of the manipulation chip is performed in the direction from one main groove 31 to multiple branching grooves 32, it is possible to perform a multi-item manipulation on one sample. For instance, the nucleic acid extraction and nucleic acid purification may be performed in the main groove 31, the group of magnetic particles may be separated into a plurality of groups at the branch points of the grooves, and the PCR analysis using different primers may be performed in the respective branching grooves 32.

[8-2-1. Case of Using One Magnet]

Figure 15:
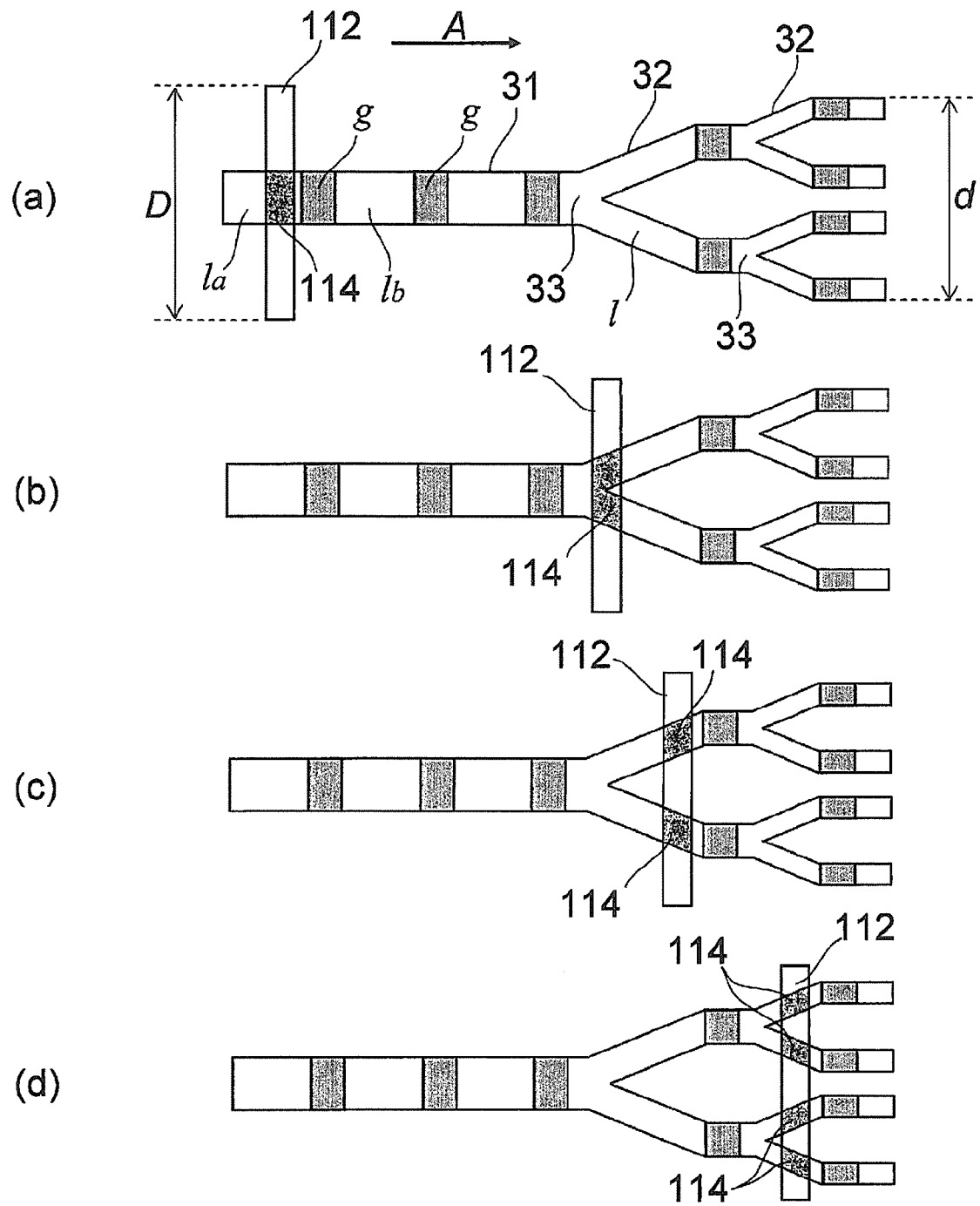
FIG. 15 shows a schematic plan view of an example of a method of dividing a magnetic particle group at branch points of the groove when using the manipulation chip having the branching groove.

In an example of the method for separating the group of magnetic particles at the branch points, as shown in FIG. 15, the magnet 112 is used, which has a length D equal to or greater than a maximum branch width d (i.e. maximum width of the entirety of the branching grooves 32) in a direction substantially perpendicular to a traveling direction A. The magnet 112 is positioned so that the length D is in the direction substantially perpendicular to the traveling direction A, and is moved in the traveling direction A (FIG. 15a). When the magnet 112 passes through the branch point, the group of magnetic particles is separated following the branching grooves (FIG. 15b). After the group of magnetic particles is completely separated, the magnet 112 is moved further (FIG. 15c), and the magnetic particles are further separated into groups at next branch points. At last, the magnetic particles are separated into groups of the same number as the maximum branch number of the branching grooves (FIG. 15d). Thus, the target substance adsorbed on the magnetic particles can be divided into a plurality of aliquots.

Since one magnet 112 is used in this embodiment, all the groups of magnetic particles are moved at the same time and at the same speed.

In order to separate the magnetic particles into groups of approximately equal number at the branch points, it is preferred to dispose the branching grooves symmetrically with respect to a center line of the longitudinal direction of the groove. For example, the branching grooves 32 are disposed symmetrically with respect to the center line of the longitudinal direction of the main groove 31. The branching grooves that branch further from branching grooves are disposed in the same manner.

To facilitate the division of the magnetic particles, it is preferred to branch the branching grooves 32 at an acute angle. For separating the magnetic particles easily, a partition plate (not shown) may also be provided in a phase 33 located at the branch point (aqueous liquid phase in this case). The partition plate is preferred particularly when a branch angle is greater than an acute angle.

[8-2-2. Case of Using Multiple Magnets]

Figure 16:
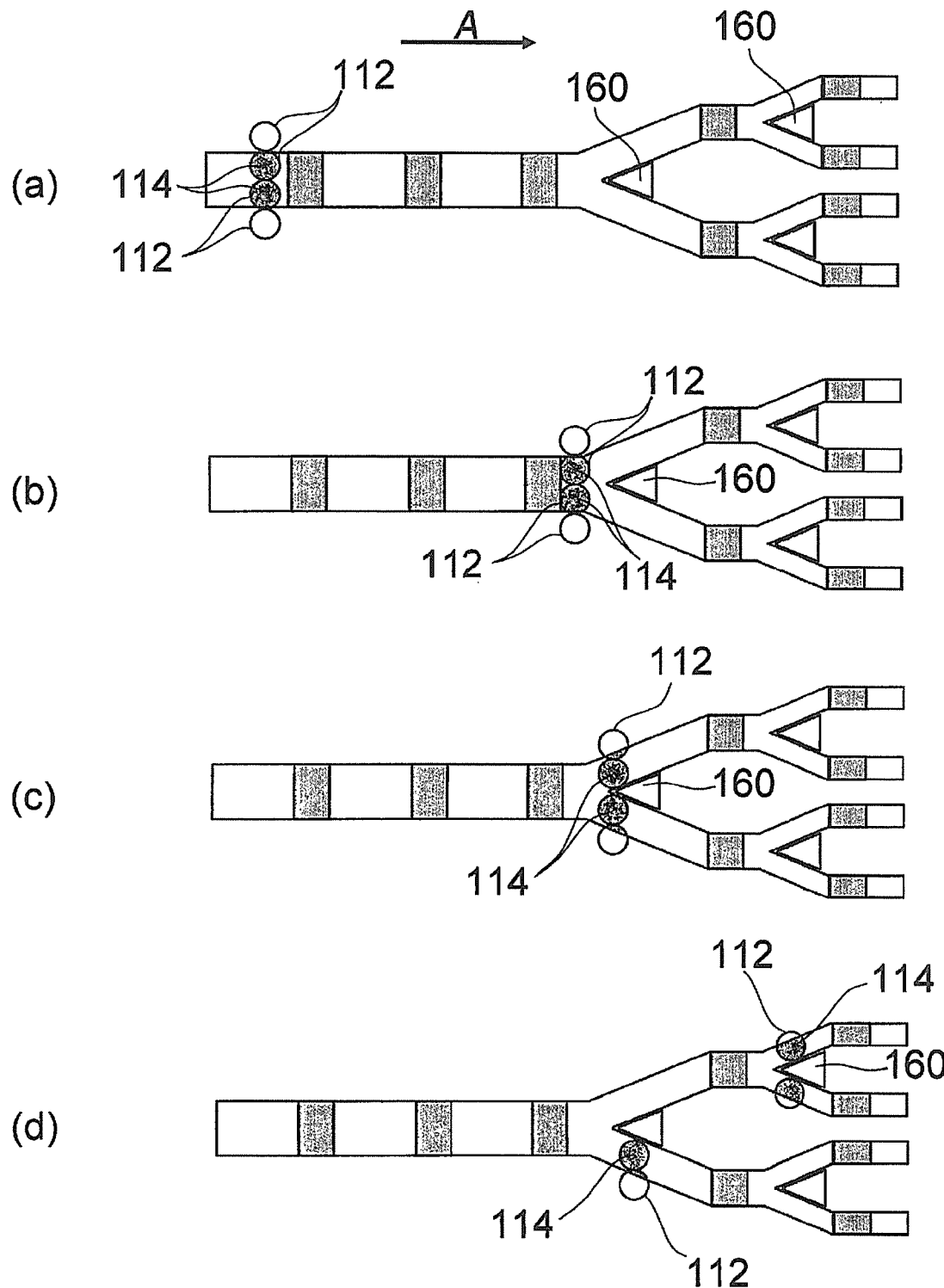
FIG. 16 shows a schematic plan view of an example of the method of dividing the magnetic particle group at branch points of the groove when using the manipulation chip having the branching groove.

In another example of the method for separating the group of magnetic particles at the branch points, as shown in FIG. 16, a plurality of magnets 112 may be used, and the number of the magnets 112 is at least equal to the maximum branch number. The magnets 112 may be disposed in a one-dimensional array (specifically, arranged in the direction substantially perpendicular to the traveling direction A) or a two-dimensional array, as illustrated. Moreover, a separation auxiliary tool 160 capable of separating the magnets attracted each other may be provided in the path of the magnets at the branch points between the main groove and the branching grooves.

When four magnets 112 that are attracted to each other are moved in the traveling direction A (FIG. 16a) and come near the branch point (FIG. 16b), the mass of the magnets 112 is separated into two magnet masses (FIG. 16c) by the separation auxiliary tool 160 disposed at the branch point. While the mass of the magnets 112 is separated, the group of magnetic particles 114 is also separated. In this embodiment, the manipulation can be performed independently for each branching groove. That is to say, after the separation, one of the masses of the magnets 112 may be left in one of the branching grooves while the other one of the masses of the magnets 112 is moved along the other branching groove (FIG. 16d). Thus, the groups of magnetic particles 114 can be moved along with the magnets 112 independently in the respective branching grooves.

Figure 17:
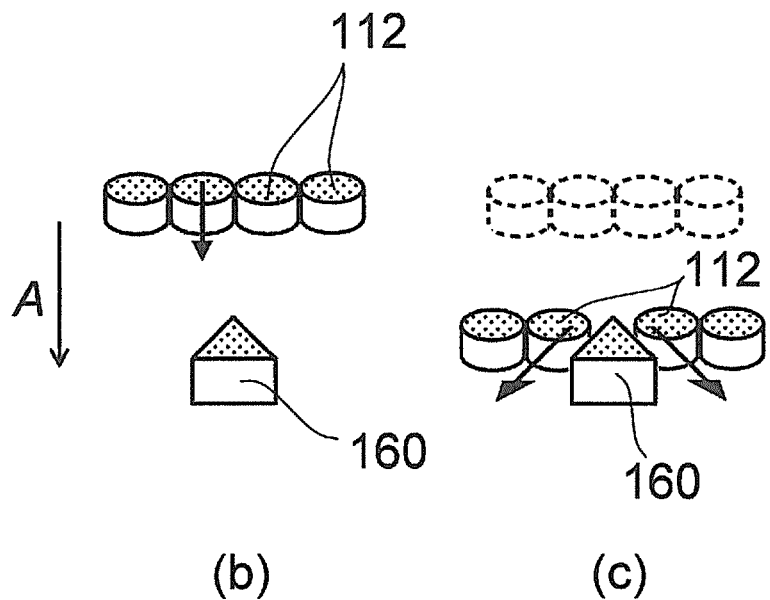
FIG. 17 schematically shows a mechanism for separating a plurality of magnets attracted to each other with a separation auxiliary tool at the branch points of the groove in the example of FIG. 16, wherein the processes b and c are respectively equivalent to the processes b and c and FIG. 16.
Figure 18:
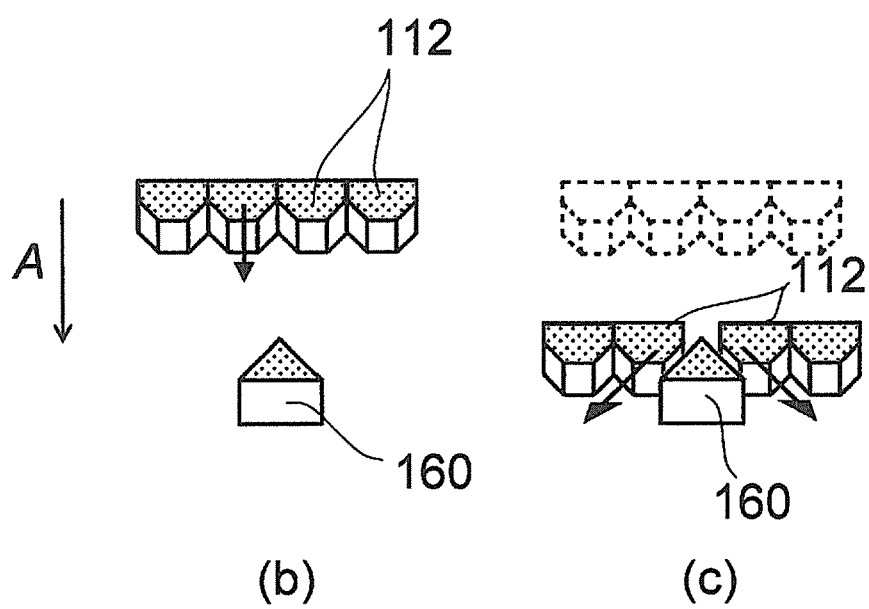
FIG. 18 shows a modified example of the planar shape of the magnet of FIG. 17.
Figure 19:
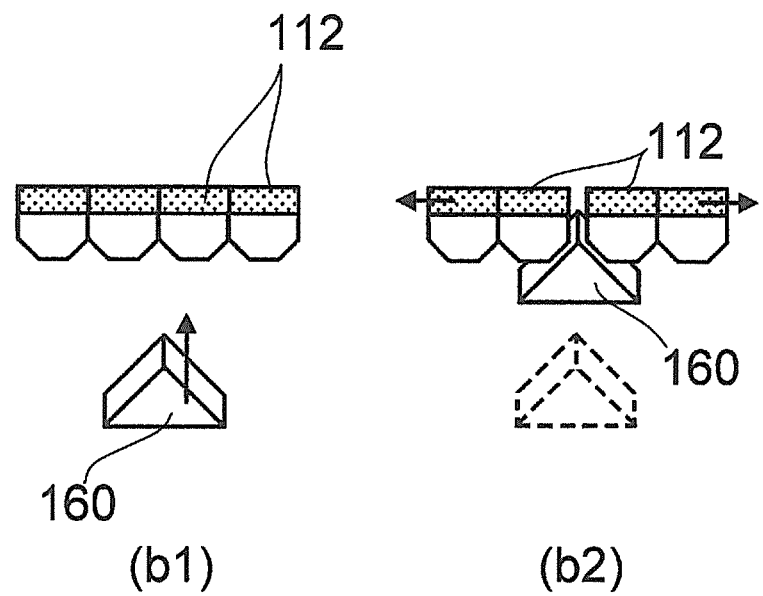
FIG. 19 shows a modified example of the mechanism for separating the plurality of magnets attracted to each other with the separation auxiliary tool at the branch points of the groove.

A mechanism for separating the magnets is explained with reference to FIGS. 17 to 19. FIGS. 17 to 19 respectively show the magnets 112 and the separation auxiliary tool 160, but the other elements, such as the manipulation chip and the magnetic particles, are omitted. The meshed surfaces of the magnets 112 and the separation auxiliary tool 160 indicate that these surfaces are on a plane substantially parallel to the substrate surface of the manipulation chip (which is the lower surface of the substrate, for example, hereinafter) and are substantially on the same plane, for example. In addition, the arrows on the magnets 112 indicate their moving direction, and the arrow on the separation auxiliary tool 160 indicates its moving direction. Further, the arrow marked with "A" indicates the traveling direction (substantially parallel to the lower surface of the substrate) of the magnets in the manipulation.

Regarding the shape of the magnet 112, it is preferred that the planar shape of the magnet 112 is a circle (FIG. 17) or a polygon that may be substantially pentagonal or have more sides (FIGS. 18-19) for separating the magnets attracted to each other easily.

Regarding the shape of the separation auxiliary tool 160, it is preferred that the shape can help to push the separation auxiliary tool 160 through the magnets attracted to each other and can sufficiently pull the magnets apart, so as to separate the magnets attracted to each other. For example, a portion of the separation auxiliary tool (i.e., the portion to be pushed through the magnets) is preferably formed in an acute-angle cross-sectional shape. Specifically, the above portion may be wedge-shaped.

FIG. 17b shows a relationship between the magnets 112 and the separation auxiliary tool 160 of FIG. 16b, and FIG. 17c shows a relationship between the magnets 112 and the separation auxiliary tool 160 of FIG. 16c. The magnets 112 and the separation auxiliary tool 160 are disposed such that the meshed surfaces are on a plane substantially parallel to the lower surface of the substrate of the manipulation chip and are for example on substantially the same plane. Moreover, the separation auxiliary tool 160 is on the traveling direction A and is fixed to the branch point of the groove not shown here. Meanwhile, the separation auxiliary tool 160 is disposed in a manner such that the portion formed to push through the magnets attracted to each other (e.g., the portion formed in the acute-angle cross-sectional shape) is oriented in a direction opposite to the traveling direction of the magnets 112.

As the magnet mass with four magnets 112 attracted to each other is moved in the traveling direction A (FIG. 17b) and reaches the separation auxiliary tool 160, the portion of the separation auxiliary tool 160 formed in the acute-angle cross-sectional shape comes between the magnets 112. When the magnet mass is moved further in the traveling direction A, the magnets 112 are gradually separated in accordance with the shape of the separation auxiliary tool 160 (FIG. 17c), and the four magnets 112 are divided into two groups each including two magnets 112.

FIG. 18 shows a modified example of the planar shape of the magnet in FIG. 17. FIG. 18b and FIG. 18c correspond to FIG. 17b and FIG. 17c, respectively.

FIG. 19 shows another modified example of the mechanism for separating the magnets at the branch point of the groove, which differs from the mechanisms of FIGS. 17 and 18. The magnets shown in FIG. 19 have the same shape as the magnets in FIG. 18, but are oriented in a different direction. In the case of FIG. 19, the magnets 112 are disposed in a manner such that the meshed surfaces are on a plane substantially parallel to the lower surface of the substrate of the manipulation chip and are for example on substantially the same plane. Moreover, the separation auxiliary tool 160 is disposed below the substrate to be close to the plane as the separation auxiliary tool 160 ascends.

When the magnet mass with four magnets 112 attracted to each other reaches a position that is substantially right below the branch point of the groove not shown here (FIG. 19b1), the separation auxiliary tool 160 is elevated below the substrate of the manipulation chip and moved toward the lower surface of the substrate. Thus, the separation auxiliary tool 160 is pushed between the magnets 112 at the position substantially right below the branch point of the groove. As the separation auxiliary tool 160 further ascends toward the lower surface of the substrate of the manipulation chip, the magnets 112 are gradually separated in accordance with the shape of the separation auxiliary tool 160 (FIG. 19b2; the four magnets 112 are divided into two groups each including two magnets 112).

Figure 20:
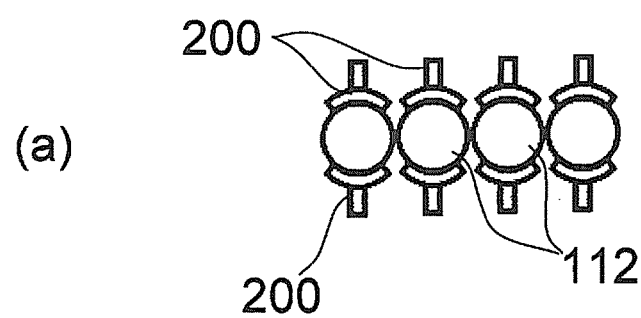
FIG. 20 schematically shows magnets provided with magnet jigs for moving the plurality of magnets in the examples of FIG. 16 and FIG. 17.
Figure 20:
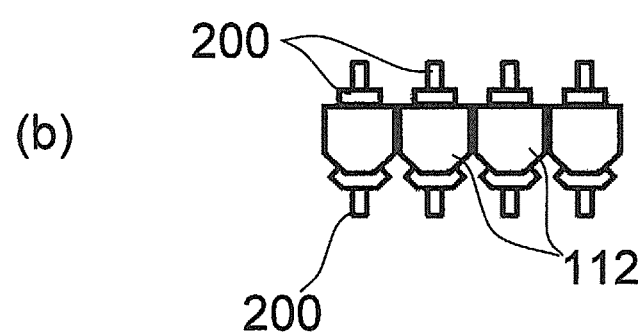

The movement of the magnets can be performed easily by clamping the magnets 112 with magnet jigs 200, as shown in FIG. 20.

[8-3. Case where Manipulation is Performed in the Direction from Multiple Branching Grooves to One Main Groove]

As shown in FIG. 3b-c and FIG. 4b, for example, if the manipulation of the manipulation chip is performed in the direction from multiple branching grooves 32 to one main groove 31, the treatments in the branching grooves 32 can be individualized while the common treatment can be carried out in the main groove 31. In the common treatment, detection by means of the detection means 35, as schematically shown in FIG. 3c, can be performed, for example.

In an example, the samples obtained through the treatments in the respective branching grooves 32 may be mixed in the main groove 31 to be supplied to a treatment such as s reaction, etc. In such case, one magnet, as described in 8-2-1, may be used to move from the side of the branching grooves 32 to the side of the main groove 31, so as to simultaneously move the samples in the branching grooves 32 and integrate the same.

In another example, different samples may be respectively processed in the branching grooves 32, and the obtained different samples may not be mixed but separately supplied to the same treatment, such as a reaction, a detection or an analysis, etc., in the main groove 31. In such a case, each branching groove 32 is provided with a magnet, which is moved independently from the side of the branching grooves 32 to the side of the main groove 31, so as to manipulate the samples in the branching grooves 32 individually.

Branching grooves that further branch from a branching groove 34 shown in FIG. 3c can accommodate a reagent or cleaning solution, etc. For instance, the branching grooves may accommodate different types of reagents that are not provided in the branching grooves 32 according to the use of the manipulation chip. The reagents, etc., can be transported to the main groove by the magnetic particles.

[8-4. Case where Multiple Grooves Intersect Each Other]

If multiple grooves intersect each other as shown in FIG. 5, the sample can move freely in the intersecting grooves. Therefore, when multiple samples are manipulated, for example, a portion of the samples can be divided. In addition, when multiple samples are manipulated, the common treatment can be performed on a part of the samples. In this way, the samples can be divided or made common freely.

Further, by disposing multiple grooves to intersect each other, many phases are accommodated in the substrate having a small area. Hence, it is possible to integrate many treatments of reaction, detection and analysis, etc.

What is claimed is:

1. A chip device adapted for manipulating an object component, comprising:
   a manipulation chip comprising a substrate, a groove formed in a surface of the substrate, a plurality of opening sections communicating with the groove, and a manipulation medium accommodated in the groove connected between the opening sections such that gel phases and aqueous liquid phases are alternately arranged in a longitudinal direction of the groove and are in contact with each other, wherein the gel phases and the aqueous liquid phases are in contact also on two sidewalls of the groove, and the aqueous liquid phases are secured by the gel phases;
   magnetic particles for capturing and transporting the object component; and
   a magnetic field application device capable of moving the magnetic particles in the longitudinal direction of the groove in the substrate by applying a magnetic field to the substrate.

2. The chip device of claim 1, wherein among the aqueous liquid phases, the aqueous liquid phase accommodated at a position closest to one end or the other end of the groove is to be initially supplied with a sample containing the object component.

3. The chip device of claim 1, wherein the groove is composed of a main groove and a branching groove that branches from the main groove.

4. The chip device of claim 3, wherein the aqueous liquid phase accommodated at a position closest to the end of the groove on the main groove side is to be initially supplied with the object component.

5. The chip device of claim 3, wherein the aqueous liquid phase accommodated at a position closest to the end of the groove on the branching groove side is to be initially supplied with the object component.

6. The chip device of claim 3, wherein
   the magnetic field application device comprises a plurality of magnets that are substantially parallel to the surface of the substrate, and are disposed in a one-dimensional array or a two-dimensional array,
   in a state that the plurality of magnets are attracted to each other, the plurality of magnets are movable substantially parallel to the surface of the substrate and in the longitudinal direction of the main groove, and
   a separation auxiliary tool is disposed on a path of the magnets and at a branch point between the main groove and the branching groove for separating the plurality of magnets.

7. The chip device of claim 1, wherein the groove is composed of a plurality of grooves that intersect each other in a grid pattern.

8. The chip device of claim 1, wherein a portion of a surface of the groove, which is in contact with the gel phases, has been subjected to a hydrophobic treatment.

9. The chip device of claim 1, wherein a portion of the surface of the groove, which is in contact with the aqueous liquid phases, has been subjected to a hydrophilic treatment.

10. The chip device of claim 1, wherein the groove has a width of 0.005 mm to 10 mm and a depth of 0.005 mm to 5 mm.

11. The chip device of claim 1, wherein a cover is provided on the surface of the substrate on the side where the groove is formed.

12. The chip device of claim 11, wherein the cover comprises a hole that penetrates the cover to communicate with the gel phase located at at least one end of the groove.

13. The chip device of claim 1, wherein the aqueous liquid phases comprise a phase selected from the group consisting of a nucleic acid extraction solution phase, a nucleic acid cleaning solution phase, and a nucleic acid amplification reaction solution phase.

14. A method for manufacturing a manipulation chip included in the chip device of claim 1, comprising the following processes:
   (i) a process of preparing a gel phase section in which a plurality of gel blocks are disposed apart from each other in the longitudinal direction of the groove formed in the substrate; and
   (ii) a process of preparing an aqueous liquid phase section by disposing an aqueous liquid in a groove space adjacent to the gel phase section.

15. The method of claim 14, further comprising: (iii) a process of disposing the cover on the surface of the substrate on the side where the groove is formed.

16. A method for manipulating the object component with use of the chip device of claim 1, comprising the following processes:
   (i) a process of obtaining an aqueous liquid mixture comprising a sample that contains the object component, magnetic particles, and the aqueous liquid in the aqueous liquid phase located at one end of the manipulation chip;
   (ii) a process of generating a magnetic field by the magnetic field application device and transporting the magnetic particles together with the object component from the phase of the aqueous liquid mixture at an endmost position to the adjacent aqueous liquid phase through the gel phase;
   (iii) a process of performing a first desired treatment in the aqueous liquid phase;
   (iv) a process of generating a magnetic field by the magnetic field application device and transporting the magnetic particles together with the object component from the aqueous liquid phase to another aqueous liquid phase;
   (v) a process of performing a second desired treatment in the another aqueous liquid phase;
   (vi) a process of reiterating the processes (iv) and (v) as required; and
   (vii) a process of transporting the magnetic particles together with the object component to the aqueous liquid phase located at the other end of the manipulation chip.

17. The method of claim 16, wherein a plurality of manipulation chips are provided, and the transportation is performed simultaneously by the magnetic particles in the plurality of manipulation chips.

18. The method of claim 16, wherein the object component is a nucleic acid; and
   in the process (i), the aqueous liquid contained in the aqueous liquid mixture in the phase located at the one end is a liquid that releases the nucleic acid and binds or adheres the nucleic acid to the magnetic particles, and nucleic acid extraction is performed in the aqueous liquid; and
   in the processes (ii) to (vi), at least one of the aqueous liquid phases comprises a cleaning solution for the magnetic particles, and nucleic acid purification is performed by removing impurities that accompany the released nucleic acid in the cleaning solution.

19. The method of claim 18, wherein in the process (vii), the aqueous liquid phase located at the other end comprises a nucleic acid amplification reaction solution, and amplification of a target nucleic acid in the purified nucleic acid is performed in the nucleic acid amplification reaction solution.

20. The method according to claim 19, wherein a product of the nucleic acid amplification reaction is detected in real time.

* * * * *